United States Patent [19]

Anthony et al.

[11] Patent Number: 5,602,076
[45] Date of Patent: Feb. 11, 1997

[54] CERTAIN FUNGICIDES, PESTICIDES AND PLANT GROWTH REGULANTS

[75] Inventors: Vivienne M. Anthony, Maidenhead; John M. Clough, Marlow; Paul DeFraine, Wokingham; Christopher R. A. Godfrey, Bracknell, all of England

[73] Assignee: Zeneca Limited, London, England

[21] Appl. No.: 412,450

[22] Filed: Mar. 29, 1995

Related U.S. Application Data

[63] Continuation of Ser. No. 239,845, May 9, 1994, Pat. No. 5,470,819, which is a continuation of Ser. No. 738,311, Jul. 31, 1991, abandoned, which is a division of Ser. No. 465,526, Jan. 17, 1990, Pat. No. 5,057,146, which is a continuation of Ser. No. 39,252, Apr. 17, 1987, abandoned.

[30] Foreign Application Priority Data

Apr. 17, 1986 [GB] United Kingdom ............ 8609454
Dec. 23, 1986 [GB] United Kingdom ............ 8630825

[51] Int. Cl.$^6$ .................. C07D 239/22; A01N 43/54
[52] U.S. Cl. .................. 504/239; 514/256; 544/298; 544/318; 544/225
[58] Field of Search .................. 546/294, 296, 546/300, 301, 302; 544/298, 318, 225; 504/244, 239; 514/256

[56] References Cited

U.S. PATENT DOCUMENTS

4,254,262  3/1981  Koike .................. 546/287

FOREIGN PATENT DOCUMENTS

3916678  8/1981  Australia .................. 544/315
203606  12/1989  European Pat. Off. .................. 560/60
203608  12/1989  European Pat. Off. .................. 560/60

Primary Examiner—Alan L. Rotman
Attorney, Agent, or Firm—Cushman Darby & Cushman IP Group Pillsbury Madison & Sutro LLP

[57] ABSTRACT

This invention relates to derivatives of acrylic acid useful in agriculture (especially as fungicides but also as plant growth regulators, insecticides and nematocides), to processes for preparing them, to agricultural (especially fungicidal compositions containing them, and to methods of using them to combat fungi, especially fungal infections in plants, to regulate plant growth and to kill or control insect or nematode pests.

The invention provides a compound having the formula (I):

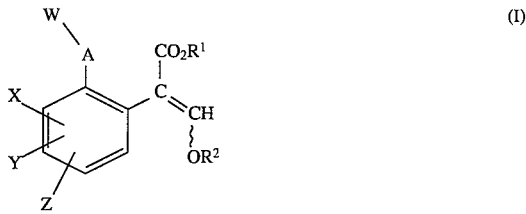

and stereoisomers thereof, wherein W is a substituted pyridinyl or substituted pyrimidinyl group linked to A by any of its ring carbon atoms; A is either an oxygen atom or $S(O)_n$ wherein n is 0, 1 or 2; X, Y and Z, which are the same or different, are hydrogen or halogen atoms, or hydroxy, optionally substituted alkyl (including haloalkyl), optionally substituted alkenyl, optionally substituted alkynyl, optionally substituted alkoxy, (including haloalkoxy), optionally substituted alkylthio, optionally substituted aryloxy, optionally substituted arylalkoxy, optionally substituted acyloxy, optionally substituted amino, optionally substituted acylamino, nitro, cyano, —$CO_2R^3$, —$CONR^4R^5$, —$COR^6$ or —$S(O)_mR^7$ (wherein m is 0, 1 or 2) groups, or any two of the groups X, Y and Z, when they are in adjacent positions on the phenyl ring, may join to form a fused ring, either aromatic or aliphatic, optionally containing one or more heteroatoms; $R^1$ and $R^2$, which are the same or different, are optionally substituted alkyl (including fluoroalkyl) and the like.

14 Claims, No Drawings

CERTAIN FUNGICIDES, PESTICIDES AND PLANT GROWTH REGULANTS

This is a continuation of application Ser. No. 08/239,845, filed May 9, 1994, now U.S. Pat. No. 5,470,819 which is a continuation of application of Ser. No. 07/738,311, filed Jul. 31, 1991, now abandoned which is a divisional of application Ser. No. 07/465,526, filed Jan. 17, 1990, now U.S. Pat. No. 5,057,146 which is a continuation of application Ser. No. 07/039,252, filed Apr. 17, 1987, now abandoned.

This invention relates to derivatives of acrylic acid useful in agriculture (especially as fungicides but also as plant growth regulators, insecticides and nematocides), to processes for preparing them, to agricultural (especially fungicidal) compositions containing them, and to methods of using them to combat fungi, especially fungal infections in plants, to regulate plant growth and to kill or control insect or nematode pests.

The invention provides a compound having the formula (I):

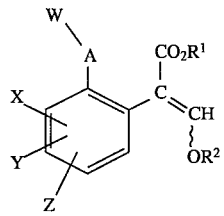

and stereoisomers thereof, wherein W is a substituted pyridinyl or substituted pyrimidinyl group linked to A by any of its ring carbon atoms; A is either an oxygen atom or $S(O)_n$ wherein n is 0, 1 or 2; X, Y and Z, which are the same or different, are hydrogen or halogen atoms, or hydroxy, optionally substituted alkyl (including haloalkyl), optionally substituted alkenyl, optionally substituted alkynyl, optionally substituted alkoxy, (including haloalkoxy), optionally substituted alkylthio, optionally substituted aryloxy, optionally substituted arylalkoxy, optionally substituted acyloxy, optionally substituted amino, optionally substituted acylamino, nitro, cyano, $-CO_2R^3$, $-CONR^4R^5$, $-COR^6$ or $-S(O)_mR^7$ (wherein m is 0, 1 or 2) groups, or any two of the groups X, Y and Z, when they are in adjacent positions on the phenyl ring, may join to form a fused ring, either aromatic or aliphatic, optionally containing one or more heteroatoms; $R^1$ and $R^2$, which are the same or different, are optionally substituted alkyl (including fluoroalkyl) groups provided that when W is 5-trifluoromethylpyridin-2-yl, A is oxygen, X is hydrogen, and $R^1$ and $R^2$ are both methyl, Y and Z are not both hydrogen, Y is not F, Cl, methyl, nitro, 5—$CF_3$, 5—$SCH_3$ or 4—$(CH_3)_2N$ if Z is hydrogen and Y and Z together are not 3-nitro-5-chloro, 3,5-dinitro, 4,5-dimethoxy or 4, 5-methylenedioxy; and $R^3$, $R^4$, $R^5$, $R^6$ and $R^7$, which are the same or different, are hydrogen atoms or optionally substituted alkyl, optionally substituted cycloalkyl, optionally substituted cycloalkylalkyl, optionally substituted alkenyl, optionally substituted alkynyl, optionally substituted aryl or optionally substituted aralkyl groups; and metal complexes thereof.

The compounds of the invention contain at least one carbon-carbon double bond, and are sometimes obtained in the form of mixtures of geometric isomers. However, these mixtures can be separated into individual isomers, and this invention embraces such isomers and mixtures thereof in all proportions including those which consist substantially of the (Z)-isomer and those which consist substantially of the (E)-isomer.

The individual isomers which result from the unsymmetrically substituted double bond of the acrylate group are identified by the commonly used terms "E" and "Z". These terms are defined according to the Cahn-Ingold-Prelog system which is fully described in the literature (see, for example, J March, "Advanced Organic Chemistry," 3rd edition, Wiley-Interscience, page 109 et seq).

Usually one isomer is more fungicidally active then the other; the more active isomer being the one in which the group $-OR^2$ is on the same side of the double bond as the phenyl ring. In the case of the compounds of the present invention this is the (E)-isomer. The (E)-isomers form a preferred embodiment of the invention.

The formula:

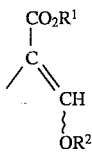

used hereinafter signifies a separable mixture of both geometric isomers about the acrylate double bond, i.e.

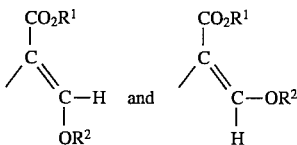

Alkyl groups, wherever present as a group or moiety in, for example, "alkoxy", "alkylthio" and "aralkyl", can be in the form of straight or branched chains, and contain preferably 1 to 6, more preferably 1 to 4, carbon atoms; examples are methyl, ethyl, propyl, (n- or iso-propyl) and butyl (n-, sec-, iso- or t-butyl).

$R^1$ and $R^2$, which are optionally substituted alkyl groups, are preferably optionally substituted $C_{1-4}$, particularly $C_{1-2}$, alkyl groups. A preferred substituent is fluorine of which one or more atoms may be present. It is particularly preferred that $R^1$ and $R^2$ are both methyl, either one or both methyl groups being optionally substituted by one, two or three fluorine atoms.

Halogen atoms, wherever referred to are particularly fluorine, chlorine or bromine atoms and especially fluorine or chlorine atoms.

Cycloalkyl is preferably $C_{3-6}$ cycloalkyl, for example cyclohexyl, and cycloalkylalkyl is preferably $C_{3-6}$ cycloalkyl($C_{1-4}$)alkyl, for example, cyclopropylethyl. Alkenyl and alkynyl groups preferably contain 2 to 6, more preferably 2 to 4, carbon atoms in the form of straight or branched chains. Examples are ethenyl, allyl and propargyl. Aryl is preferably phenyl and aralkyl is preferably benzyl, phenylethyl or phenyl n-propyl. Optionally substituted alkyl includes in particular, haloalkyl, hydroxyalkyl, alkoxyalkyl, optionally substituted aralkyl, especially optionally substituted phenylalkyl, and optionally substituted aryloxyalkyl, especially optionally substituted phenoxyalkyl; optionally substituted alkenyl includes optionally substituted phenylalkenyl, especially optionally substituted phenylethenyl; optionally substituted aryloxy includes optionally substituted phenyloxy; and optionally substituted arylalkoxy includes optionally substituted benzyloxy. Optional substituents for "alkoxy" and "alkylthio" include those described above for "alkyl".

Substituents which may be present in any optionally substituted aryl or heteroaryl moiety include one or more of the following; halogen, hydroxy, $C_{1-4}$ alkyl (especially methyl and ethyl), $C_{1-4}$ alkoxy (especially methoxy), halo($C_{1-4}$)alkyl(especially trifluoromethyl), halo ($C_{1-4}$)alkoxy (especially trifluoromethoxy), $C_{1-4}$ alkylthio (especially methylthio), ($C_{1-4}$)alkoxy($C_{1-4}$)alkyl, $C_{3-6}$ cycloalkyl, $C_{3-6}$ cycloalkyl($C_{1-4}$)alkyl, aryl (especially phenyl), aryloxy (especially phenyloxy), aryl($C_{1-4}$)alkyl (especially benzyl, phenylethyl and phenyl n-propyl), aryl $C_{1-4}$ alkoxy (especially benzyloxy), aryloxy($C_{1-4}$)alkyl (especially phenyloxymethyl), acyloxy (especially acetyloxy and benzoyloxy), cyano, thiocyanato, nitro, —NR'R", —NHCOR', —NHCONR'R", —CONR'R", —COOR', —OSO₂R', —SO₂R', —COR', —OCOR', —CR'=NR" or —N=CR'R" in which R' and R" are independently hydrogen, $C_{1-4}$alkyl, $C_{1-4}$alkoxy, $C_{1-4}$ alkylthio, $C_{3-6}$ cycloalkyl, $C_{3-6}$ cycloalkyl($C_{1-4}$)alkyl, phenyl or benzyl, the phenyl and benzyl groups being optionally substituted with halogen, $C_{1-4}$ alkyl or $C_{1-4}$ alkoxy. Optionally substituted amino, acylamino and acyloxy groups include the groups —NR'R", —NHCOR' and —OCOR' in which R' and R" are as defined above.

The substituents on the substituted pyridinyl or substituted pyrimidinyl ring W, which are the same or different, include any of the values given for X, Y and Z. In particular, they include halogen atoms, or hydroxy, optionally substituted alkyl (including haloalkyl), especially $C_{1-4}$ alkyl, optionally substituted alkenyl, especially $C_3$–$C_4$ alkenyl, optionally substituted aryl, optionally substituted alkynyl, especially $C_3$–$C_4$ alkynyl, optionally substituted alkoxy (including haloalkoxy), especially $C_{1-4}$ alkoxy, optionally substituted aryloxy, optionally substituted heterocyclyloxy, (especially heteroaryloxy), optionally substituted aryl, optionally substituted heterocyclyl, (especially 5- and 6-membered carbon-nitrogen rings e.g.

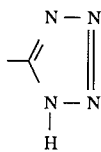

nitro, cyano, —NR'R", —NHCOR', —CONR'R", —OCOR', —CO₂R', —COR', —CH=NOR", —CH₂NR'R", —CH₂OR', —CH₂NHCOR', —CH₂OCOR', or S(O)$_m$R' (wherein m is 0, 1 or 2) groups or any two of the substituents on the pyridinyl or pyrimidinyl rings, when they are in adjacent positions on the ring may join to form an optionally substituted fused ring, either aromatic or aliphatic, optionally containing one or more heteroatoms; and R', R", R³, R⁴, R⁵, R⁶ and R⁷ are as defined above.

Pyridines and pyrimidines with hydroxy substituents in appropriate positions may also exist in the corresponding tautomeric oxo-forms, i.e. as the corresponding pyridones and pyrimidones, respectively. It is intended that when there is a hydroxy substituent on the pyridinyl or pyrimidinyl ring W the present invention should include all such tautomeric forms and mixtures thereof (see, for example, G R Newkome and W W Paudler, *Contemporary Heterocyclic Chemistry*, Wiley—Interscience pp236–241).

Preferred substituent haloalkyl and haloalkoxy groups are halo $C_{1-4}$ alkyl and halo ($C_{1-4}$)alkoxy groups. Haloalkyl includes particularly trihalomethyl and especially trifluoromethyl (except where otherwise indicated). Preferred aryl groups, or moieties, [e.g. as in aryloxy] are phenyl whilst substituents on a substituted amino group, or moiety are preferably $C_{1-4}$ alkyl.

Preferred heterocyclic groups, or moieties (e.g. as in heterocyclyl or heterocyclyloxy) are, for example, 2-, 3-, or 4-optionally substituted pyridines or 2-, 4- or 5-optionally substituted pyrimidines.

In one particular aspect, the invention provides compounds having the formula (I):

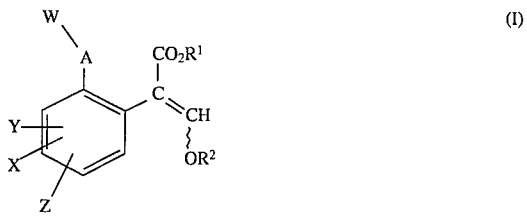

and stereoisomers thereof, wherein W is a substituted pyridinyl or a substituted pyrimidinyl group linked to A by any one of its carbon atoms and bearing substituents as defined above; A is either an oxygen atom or S(O)$_n$ wherein n is 0, 1 or 2; X, Y and Z, which are the same or different, are hydrogen, fluorine, chlorine or bromine atoms, or hydroxy, $C_{1-4}$ alkyl, $C_{2-5}$ alkenyl, $C_{2-5}$ alkynyl, phenyl, $C_{1-4}$ haloalkyl, $C_{1-4}$ alkoxy, phenoxy, benzyloxy or mono- or dialkylamino groups, or any two of the groups X, Y and Z, when they are in adjacent positions on the phenyl ring, join to form a fused aromatic ring; wherein the aliphatic moieties of any of the foregoing are optionally substituted with one or more $C_{1-4}$ alkoxy groups, fluorine, chlorine or bromine atoms, phenyl rings which themselves are optionally substituted, heterocyclic rings which are either aromatic or non-aromatic and are themselves optionally substituted, nitro, amino, cyano, hydroxyl or carboxyl groups, and wherein the phenyl moieties of any of the foregoing are optionally substituted with one or more fluorine, chlorine or bromine atoms, phenyl rings, $C_{1-4}$ alkyl, $C_{1-4}$ alkoxy, cyano, amino, nitrile, hydroxyl or carboxyl groups; and R¹ and R², which are the same or different, are $C_{1-4}$ alkyl (especially both methyl), each optionally substituted with one, two or three halogen (especially fluorine), atoms provided that when W is 5-trifluoromethylpyridin-2-yl, A is oxygen, X is hydrogen, and R¹ and R² are both methyl, Y and Z are not both hydrogen, Y is not F, Cl, methyl, nitro, 5—CF₃, 5—SCH₃ or 4—(CH₃)₂N if Z is hydrogen and Y and Z together are not 3-nitro-5-chloro, 3,5-dinitro, 4,5-dimethoxy or 4, 5-methylenedioxy.

When one or more of X, Y and Z are other than hydrogen it is preferred that they are single atoms or sterically small groups such as fluorine, chlorine, bromine, hydroxy, methyl, methoxy, trifluoromethyl, methylamino and dimethylamino. It is further preferred that one of such substituents occupies the 5-position of the phenyl ring (the acrylate group being attached to the 1-position) as this may offer advantages with respect to phytotoxicity especially where there is present only a single substituent such as chlorine.

In another aspect the invention provides compounds having the formula (Ia):

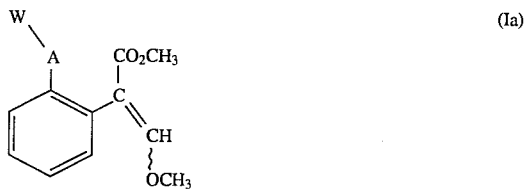

and stereoisomers thereof, wherein A is S(O)$_n$ wherein n is 0, 1 or 2, or preferably, an oxygen atom; W is a substituted pyridinyl or a substituted pyrimidinyl group linked to A by any one of its carbon atoms, the substituents on the pyridinyl or pyrimidinyl rings, which are the same or different, being one or more halogen atoms, or hydroxy, optionally substituted alkyl (including haloalkyl), optionally substituted alkenyl, optionally substituted aryl, optionally substituted alkynyl, optionally substituted alkoxy, (including haloalkoxy), optionally substituted aryloxy, optionally substituted heterocyclyloxy, optionally substituted aryl, optionally substituted heterocyclyl, optionally substituted acyloxy, optionally substituted amino, optionally substituted acylamino nitro cyano —$CO_2R^3$, —$CONR^4R^5$, —$COR^6$ or $S(O)_mR^7$ (wherein m=0, 1 or 2) groups; provided that when W is 5-trifluoromethylpyridin-2-yl, A is oxygen, X is hydrogen, and $R^1$ and $R^2$ are both methyl, Y and Z are not both hydrogen, Y is not F, Cl, methyl, nitro, 5—$CF_3$, 5—$SCH_3$ or 4—$(CH_3)_2N$ if Z is hydrogen and Y and Z together are not 3-nitro-5-chloro, 3,5-dinitro, 4, 5-dimethoxy or 4, 5-methylenedioxy; and $R^3$, $R^4$, $R^5$, $R^6$ and 7 are as defined above.

Preferred substituents on the pyridinyl or pyrimidinyl ring are chlorine, fluorine, bromine, methyl, trifluoromethyl (except where otherwise indicated), trichloromethyl and methoxy.

In a still further aspect the invention provides compounds having the formula (Ib):

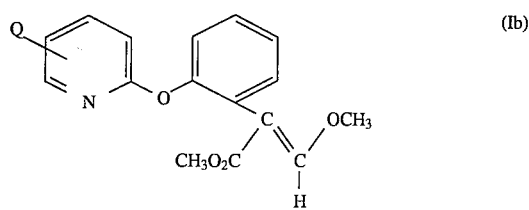

(Ib)

where Q is methyl, trifluoromethyl (but not 5-trifluoromethyl), methoxy, bromine, fluorine or, especially, chlorine.

Q is preferably in the 4-, 5- or 6- position of the pyridine ring, and more preferably in the 4- position when it is methyl, for instance.

The invention is illustrated by the compounds presented in Tables I to III below.

TABLE I

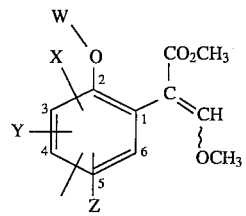

| Compound No. | W | X | Y | Z | Melting Point (°C.) | Olefinic* | Isomer + |
|---|---|---|---|---|---|---|---|
| 1 | 3'-Fluoropyridin-2'-yl | H | H | H | | | E |
| 2 | 3'-Chloropyridin-2'-yl | H | H | H | | | E |
| 3 | 3'-Bromopyridin-2'-yl | H | H | H | | | E |
| 4 | 3'-Methylpyridin-2'-yl | H | H | H | | | E |
| 5 | 3'-(Trifluoromethyl)pyridin-2'-yl | H | H | H | | | E |
| 6 | 3'-Methoxypyridin-2'-yl | H | H | H | | | E |
| 7 | 4'-Fluoropyridin-2'-yl | H | H | H | | | E |
| 8 | 4'-Chloropyridin-2'-yl | H | H | H | | | E |
| 9 | 4'-Bromopyridin-2'-yl | H | H | H | | | E |
| 10 | 4'-Methylpyridin-2'-yl | H | H | H | gum | 7.37 | E |
| 11 | 4'-(Trifluoromethyl)pyridin-2'-yl | H | H | H | gum | 7.44 | E |
| 12 | 4'-Methoxypyridin-2'-yl | H | H | H | | | E |
| 13 | 5'-Fluoropyridin-2'-yl | H | H | H | | | E |
| 14 | 5'-Chloropyridin-2'-yl | H | H | H | 77–8 | 7.41 | E |
| 15 | 5'-Bromopyridin-2'-yl | H | H | H | 104.6–105.4 | 7.43 | E |
| 16 | 5'-Methylpyridin-2'-yl | H | H | H | gum | 7.42 | E |
| 17 | 5'-Methoxypyridin-2'-yl | H | H | H | | | E |
| 18 | 6'-Fluoropyridin-2'-yl | H | H | H | | | E |
| 19 | 6'-Chloropyridin-2'-yl | H | H | H | | | E |
| 20 | 6'-Bromopyridin-2'-yl | H | H | H | | | E |
| 21 | 6'-Methylpyridin-2'-yl | H | H | H | gum | 7.40 | E |
| 22 | 6'-(Trifluoromethyl)pyridin-2'-yl | H | H | H | gum | 7.42 | E |
| 23 | 6'-Methoxypyridin-2'-yl | H | H | H | | | E |
| 24 | 2'-Fluoropyridin-3'-yl | H | H | H | | | E |
| 25 | 2'-Chloropyridin-3'-yl | H | H | H | | | E |
| 26 | 2'-Bromopyridin-3'-yl | H | H | H | | | E |
| 27 | 2'-Methylpyridin-3'-yl | H | H | H | | | E |
| 28 | 2'-(Trifluoromethyl)pyridin-3'-yl | H | H | H | | | E |
| 29 | 2'-Methoxypyridin-3'-yl | H | H | H | | | E |
| 30 | 4'-Fluoropyridin-3'-yl | H | H | H | | | E |
| 31 | 4'-Chloropyridin-3'-yl | H | H | H | | | E |
| 32 | 4'-Bromopyridin-3'-yl | H | H | H | | | E |
| 33 | 4'-Methylpyridin-3'-yl | H | H | H | | | E |
| 34 | 4'-(Trifluoromethyl)pyridin-3'-yl | H | H | H | | | E |
| 35 | 4'-Methoxypyridin-3'-yl | H | H | H | | | E |
| 36 | 5'-Fluoropyridin-3'-yl | H | H | H | | | E |
| 37 | 5'-Chloropyridin-3'-yl | H | H | H | | | E |
| 38 | 5'-Bromopyridin-3'-yl | H | H | H | | | E |
| 39 | 5'-Methylpyridin-3'-yl | H | H | H | | | E |
| 40 | 5'-(Trifluoromethyl)pyridin-3'-yl | H | H | H | | | E |

TABLE I-continued

| Compound No. | W | X | Y | Z | Melting Point (°C.) | Olefinic* | Isomer + |
|---|---|---|---|---|---|---|---|
| 41 | 5'-Methoxypyridin-3'-yl | H | H | H | | | E |
| 42 | 6'-Fluoropyridin-3'-yl | H | H | H | | | E |
| 43 | 6'-Chloropyridin-3'yl | H | H | H | | | E |
| 44 | 6'-Bromopyridin-3'-yl | H | H | H | | | E |
| 45 | 6'-Methylpyridin-3'-yl | H | H | H | Oil | 7.51 | E |
| 46 | 6'-(Trifluoromethyl)pyridin-3'-yl | H | H | H | | | E |
| 47 | 6'-Methoxypyridin-3'-yl | H | H | H | | | E |
| 48 | 2'-Fluoropyridin-4'-yl | H | H | H | | | E |
| 49 | 2'-Chloropyridin-4'-yl | H | H | H | | | E |
| 50 | 2'-Bromopyridin-4'-yl | H | H | H | | | E |
| 51 | 2'-Methylpyridin-4'-yl | H | H | H | | | E |
| 52 | 2'-(Trifluoromethyl)pyridin-4'-yl | H | H | H | | | E |
| 53 | 2'-Methyoxypyridin-4'-yl | H | H | H | | | E |
| 54 | 3'-Fluoropyridin-4'-yl | H | H | H | | | E |
| 55 | 3'-Chloropyridin-4'-yl | H | H | H | | | E |
| 56 | 3'-Bromopyridin-4'-yl | H | H | H | | | E |
| 57 | 3'-Methylpyridin-4'-yl | H | H | H | | | E |
| 58 | 3'-(Trifluoromethyl)pyridin-4'-yl | H | H | H | | | E |
| 59 | 3'-Methoxypyridin-4'-yl | H | H | H | | | E |
| 60 | 4'-Fluoropyrimidin-2'-yl | H | H | H | | | E |
| 61 | 4'-Chloropyrimidin-2'-yl | H | H | H | 120-121.5 | 7.40 | E |
| 62 | 4'-Bromopyrimidin-2'-yl | H | H | H | | | E |
| 63 | 4'-Methylpyrimidin-2'-yl | H | H | H | | | E |
| 64 | 4'-(Trifluoromethyl)pyrimidin-2'-yl | H | H | H | | | E |
| 65 | 4'-Methoxypyrimidin-2'-yl | H | H | H | | | E |
| 66 | 5'-Fluoropyrimidin-2'-yl | H | H | H | | | E |
| 67 | 5'-Chloropyrimidin-2'-yl | H | H | H | gum | 7.40 | E |
| 68 | 5'-Bromopyrimidin-2'-yl | H | H | H | | | E |
| 69 | 5'-Methylpyrimidin-2'-yl | H | H | H | | | E |
| 70 | 5'-(Trifluoromethyl)pyrimidin-2'-yl | H | H | H | | | E |
| 71 | 5'-Methoxypyrimidin-2'-yl | H | H | H | | | E |
| 72 | 2'-Fluoropyrimidin-4'-yl | H | H | H | | | E |
| 73 | 2'-Chloropyrimidin-4'-yl | H | H | H | | | E |
| 74 | 2'-Bromopyrimidin-4'-yl | H | H | H | | | E |
| 75 | 2'-Methylpyrimidin-4'-yl | H | H | H | | | E |
| 76 | 2'-(Trifluoromethyl)pyrimidin-4'-yl | H | H | H | | | E |
| 77 | 2'-Methoxypyrimidin-4'-yl | H | H | H | | | E |
| 78 | 5'-Fluoropyrimidin-4'-yl | H | H | H | | | E |
| 79 | 5'-Chloropyrimidin-4'-yl | H | H | H | | | E |
| 80 | 5'-Bromopyrimidin-4'-yl | H | H | H | | | E |
| 81 | 5'-Methoxypyrimidin-4'-yl | H | H | H | | | E |
| 82 | 5'-(Trifluoromethyl)pyrimidin-4'-yl | H | H | H | | | E |
| 83 | 5'-Methoxypyrimidin-4'-yl | H | H | H | | | E |
| 84 | 6'-Fluoropyrimidin-4'-yl | H | H | H | | | E |
| 85 | 6'-Chloropyrimidin-4'-yl | H | H | H | | | E |
| 86 | 6'-Bromopyrimidin-4'-yl | H | H | H | | | E |
| 87 | 6'-Methylpyrimidin-4'-yl | H | H | H | | | E |
| 88 | 6'-(Trifluoromethyl)pyrimidin-4'-yl | H | H | H | | | E |
| 89 | 6'-Methoxypyrimidin-4'-yl | H | H | H | | | E |
| 90 | 2'-Fluoropyrimidin-5'-yl | H | H | H | | | E |
| 91 | 2'-Chloropyrimidin-5'-yl | H | H | H | | | E |
| 92 | 2'-Bromopyrimidin-5'-yl | H | H | H | | | E |
| 93 | 2'-Methylpyrimidin-5'-yl | H | H | H | | | E |
| 94 | 2'-(Trifluoromethyl)pyrimidin-5'-yl | H | H | H | | | E |
| 95 | 2'-Methoxypyrimidin-5'-yl | H | H | H | | | E |
| 96 | 4'-Fluoropyrimidin-5'-yl | H | H | H | | | E |
| 97 | 4'-Chloropyrimidin-5'-yl | H | H | H | | | E |
| 98 | 4'-Bromopyrimidin-5'-yl | H | H | H | | | E |
| 99 | 4'-Methylpyrimidin-5'-yl | H | H | H | | | E |
| 100 | 4'-(Trifluoromethyl)pyrimidin-5'-yl | H | H | H | | | E |
| 101 | 4'-Methoxypyrimidin-5'-yl | H | H | H | | | E |
| 102 | 5'-(Trifluoromethyl)pyridin-2'-yl | 3-F | 5-F | H | | | E |
| 103 | 3'-Fluoro-5'-(trifluoromethyl)pyridin-2'yl | H | H | H | | | E |
| 104 | 5'-(Trifluoromethyl)pyridin-3'-yl | 4-F | H | H | | | E |
| 105 | 3',6'-Dichloro-5'-(trifluoromethyl)pyridin-2'-yl | H | H | H | | | E |

TABLE I-continued

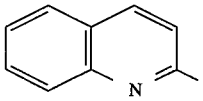

| Compound No. | W | X | Y | Z | Melting Point (°C.) | Olefinic* | Isomer + |
|---|---|---|---|---|---|---|---|
| 106 | 5',6'-Dichloro-3'-(trifluoromethyl)-pyridin-2'-yl | H | H | H | | | E |
| 107 | 5'-Chloro-3'-(trifluoromethyl)pyridin-2'-yl | H | H | H | | | E |
| 108 | 3'-Chloro-5'-(trifluoromethyl)pyridin-2'-yl | H | H | H | | | E |
| 109 | 6'-Chloro-4'-cyanopyridin-2'-yl | H | H | H | | | E |
| 110 | 3'-Cyano-5'-nitropyridin-2'-yl | H | H | H | | | E |
| 111 | 2'-Chloro-6'-fluoropyridin-4'-yl | H | H | H | | | E |
| 112 | 6'-Chloro-4'-fluoropyridin-2'-yl | H | H | H | | | E |
| 113 | 4',6'-Difluoropyridin-2'-yl | H | H | H | | | E |
| 114 | 3',5'-Dichloro-6'-fluoropyridin-2'-yl | H | H | H | | | E |
| 115 | 6'-Methoxy-3'-nitropyridin-2'-yl | H | H | H | | | E |
| 116 | 4'-Cyano-6'-fluoropyridin-2'-yl | H | H | H | | | E |
| 117 | 6'-Chloro-5'-cyanopyridin-2'-yl | H | H | H | | | E |
| 118 | 6'-Chloro-3'-cyanopyridin-2'-yl | H | H | H | | | E |
| 119 | 4'-Cyano-3',5',6'-trifluoropyridin-2'-yl | H | H | H | | | E |
| 120 | 4'-Cyano-2',5',6'-trifluoropyridin-3'-yl | H | H | H | | | E |
| 121 | 6'-Chloro,-5'-nitropyridin-2'-yl | H | H | H | | | E |
| 122 | 6'-Chloro-3'-nitropyridin-2'-yl | H | H | H | | | E |
| 123 | 5'-Cyano-6'-fluoropyridin-2'-yl | H | H | H | | | E |
| 124 | 3'-Cyano-6'-fluoropyridin-2'-yl | H | H | H | | | E |
| 125 | 4',6'-Dicyanopyridin-2'-yl | H | H | H | | | E |
| 126 | 5'-(Trichloromethyl)pyridin-2'-yl | H | H | H | | | E |
| 127 | 5'-Cyanopyridin-2'-yl | H | H | H | 108.5–109.5 | 7.45 | E |
| 128 | 5'-Bromo-4'-(trifluoromethyl)pyridin-2'-yl | H | H | H | | | E |
| 129 | 3'-Nitro-5'-(trifluoromethyl)pyridin-2'-yl | H | H | H | 113–114 | 7.41 | E |
| 130 | 5'-Formamidopyridin-2'-yl | H | H | H | gum | obscured | E |
| 131 | 5'-Aminopyridin-2'-yl | H | H | H | gum | 7.40 | E |
| 132 | 2',3',5',6'-Tetrafluoropyridin-4'-yl | H | H | H | gum | 7.55 | E |
| 133 | 5'-Nitropyridin-2'-yl | H | H | H | 107–109 | 7.45 | E |
| 134 | 4'-Methyl-5'-nitropyridin-2'-yl | H | H | H | | | E |
| 135 | 5'-(Difluoromethyl)pyridin-2'-yl | H | H | H | | | E |
| 136 | 5'-(Fluoromethyl)pyridin-2'-yl | H | H | H | | | E |
| 137 | 4',6'-Difluoropyrimidin-2'-yl | H | H | H | gum | 7.44 | E |
| 138 | 2',6'-Difluoropyrimidin-4'-yl | H | H | H | 79–80 | 7.46 | E |
| 139 | 2'-Chloro-6'-(trichloromethyl)pyrimidin-4'-yl | H | H | H | 113–114 | 7.50 | E |
| 140 | 2',6'-Dichloropyrimidin-4'-yl | H | H | H | 93–94 | 7.46 | E |
| 141 | 5'-(Methoxycarbonyl)pyridin-2'-yl | H | H | H | Oil | 7.32 | E |
| 142 | 5'-Chloro-6'-fluoropyridin-2'-yl | H | H | H | | | E |
| 143 | 5'-Chloro-6'-hydroxypyridin-2'-yl | H | H | H | | | E |
| 144 | 5'-Chloro-6'-methoxypyridin-2'-yl | H | H | H | | | E |
| 145 | 5'-Chloro-6'-cyanopyridin-2'-yl | H | H | H | | | E |
| 146 | 5',6'-Dichloropyridin-2'-yl | H | H | H | | | E |
| 147 | 6'-Bromo-5'-chloropyridin-2'-yl | H | H | H | | | E |
| 148 | 5'-Chloro-6'-acetoxypyridin-2'-yl | H | H | H | | | E |
| 149 | 5'-Bromo-6'-fluoropyridin-2'-yl | H | H | H | | | E |
| 150 | 5'-Bromo-6'-chloropyridin-2'-yl | H | H | H | | | E |
| 151 | 5'-Bromo-6'-cyanopyridin-2'-yl | H | H | H | | | E |
| 152 | 5'-Bromo-6'-hydroxypyridin-2'-yl | H | H | H | | | E |
| 153 | 5'-Bromo-6'-methoxypyridin-2'-yl | H | H | H | | | E |
| 154 | 5',6'-Dibromopyridin-2'-yl | H | H | H | | | E |
| 155 | 4'-Cyanopyridin-2'-yl | H | H | H | | | E |
| 156 | 6'-Cyanopyridin-2'-yl | H | H | H | | | E |
| 157 | 5'-Chloropyridin-2'-yl | 5-F | H | H | | | E |
| 158 | 5'-Chloropyridin-2'-yl | 3-F | 5-F | H | | | E |
| 159 | 5'-Chloropyridin-2'-yl | 4-F | 6-F | H | | | E |
| 160 | 5'-Chloropyridin-2'-yl | 4-F | 5-F | 6-F | | | E |
| 161 | 5'-Chloropyridin-2'-yl | 5-Cl | H | H | | | E |
| 161 | 5'-Chloropyridin-2'-yl | 5-CH$_3$ | H | H | | | E |
| 162 | 5'-Chloropyridin-2'-yl | 5-CH$_3$O | H | H | | | E |
| 163 | 5'-Fluoropyridin-2'-yl | 5-Cl | H | H | | | E |
| 164 | 5'-Fluoropyridin-2'-yl | 5-Cl | 3-F | H | | | E |
| 165 | | H | H | H | Oil | 7.43 | E |

TABLE I-continued

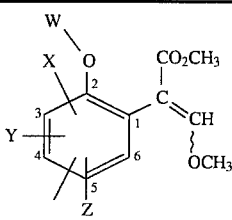

| Compound No. | W | X | Y | Z | Melting Point (°C.) | Olefinic* | Isomer + |
|---|---|---|---|---|---|---|---|
| 166 | 4'-Chloro-6'-methylpyrimidin-2'-yl | H | H | H | 115–130 | 7.44 | E |
| 167 | 2'-Chloro-6'-fluoropyridin-4'-yl | H | H | H | Oil | 7.46 | E |
| 168 | 5'-Bromo-4'-(trifluoromethyl)pyridin-2'-yl | H | H | H | | | E |
| 169 | 4',5'-Dichloropyridin-2'-yl | H | H | H | | | E |
| 170 | 4',5'-Dibromopyridin-2'-yl | H | H | H | | | E |
| 171 | 5',6'-Dichloropyridin-2'-yl | H | H | H | | | E |
| 172 | 4',6'-Dichloropyridin-2'-yl | H | H | H | | | E |
| 173 | 4',6'-Dibromopyridin-2'-yl | H | H | H | | | E |
| 174 | 5',6'-Dibromopyridin-2'-yl | H | H | H | | | E |
| 175 | 4'-Bromo-5'-chloropyridin-2'-yl | H | H | H | | | E |
| 176 | 6'-Bromo-5'-chloropyridin-2'-yl | H | H | H | | | E |
| 177 | 5'-Bromo-4'-chloropyridin-2'-yl | H | H | H | | | E |
| 178 | 5'-Bromo-6'-chloropyridin-2'-yl | H | H | H | | | E |
| 179 | 6'-Bromo-4'-chloropyridin-2'-yl | H | H | H | | | E |
| 180 | 4'-Bromo-6'-chloropyridin-2'-yl | H | H | H | | | E |
| 181 | 6'-Chloro-4'-methoxypyridin-2'-yl | H | H | H | | | E |
| 182 | 6'-Bromo-4'-methoxypyridin-2'-yl | H | H | H | | | E |
| 183 | 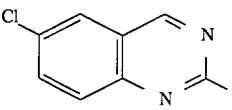 | H | H | H | | | E |
| 184 | 5'-(Benzyloxycarbonyl)pyridin-2'-yl | H | H | H | Gum | 7.39 | E |
| 185 | 4'-Formylpyridin-2'-yl | H | H | H | Oil | 7.40 | E |
| 186 | 5'-Formylpyridin-2'-yl | H | H | H | | | E |
| 187 | 6'-Formylpyridin-2'-yl | H | H | H | | | E |
| 188 | 4'-Cyanopyridin-2'-yl | H | H | H | | | E |
| 189 | 6'-Cyanopyridin-2'-yl | H | H | H | | | E |
| 190 | 5'-Hydroxymethylpyridin-2'-yl | H | H | H | | | E |
| 191 | 6'-Chloro-4'-trifluoromethylpyrid-2'-yl | H | H | H | | | E |
| 192 | 6'-Chloro-4'-trifluoromethylpyrid-2'-yl | H | H | H | | | E |
| 193 | 6'-Chloro-4'-methylpyridin-2'-yl | H | H | H | | | E |
| 194 | 2',5'-Dichloro-6'-cyanopyridin-2'-yl | H | H | H | | | E |
| 195 | 2',5'-Dichloro-6'-carboxypyridin-2'-yl | H | H | H | | | E |
| 196 | 2',5'-Dichloro-6'-methoxycarbonyl-pyridin-2'-yl | H | H | H | | | E |
| 197 | 6'-Trifluormethylpyridin-2'-yl | H | H | H | | | E |
| 198 | 6'-Methoxycarbonylpyridin-2'-yl | H | H | H | | | E |
| 199 | 6'-Carboxypyridin-2'-yl | H | H | H | | | E |
| 200 | 4'-Phenoxypyridin-2'-yl | H | H | H | | | E |
| 201 | 5'-Phenoxypyridin-2'-yl | H | H | H | | | E |
| 202 | 6'-Phenoxypyridin-2'-yl | H | H | H | | | E |
| 203 | 6'-Chloropyridin-3'-yl | H | H | H | | | E |

*Chemical shift of singlet from olefinic proton on beta-methoxyacrylate group (ppm from tetramethylsilane).
Solvent CDCl$_3$.
+ Geometry of beta-methoxyacrylate group.

TABLE II

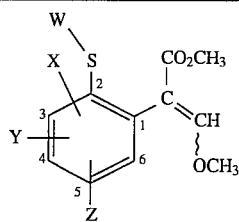

| Compound No. | W | X | Y | Z | Melting Point (°C.) | Olefinic* | Isomer + |
|---|---|---|---|---|---|---|---|
| 1 | 3'-Fluoropyridin-2'-yl | H | H | H | | | E |
| 2 | 3'-Chloropyridin-2'-yl | H | H | H | | | E |
| 3 | 3'-Bromopyridin-2'-yl | H | H | H | | | E |
| 4 | 3'-Methylpyridin-2'-yl | H | H | H | | | E |
| 5 | 3'-(Trifluoromethyl)pyridin-2'-yl | H | H | H | | | E |
| 6 | 3'-Methoxypyridin-2'-yl | H | H | H | | | E |
| 7 | 4'-Fluoropyridin-2'-yl | H | H | H | | | E |
| 8 | 4'-Chloropyridin-2'-yl | H | H | H | | | E |
| 9 | 4'-Bromopyridin-2'-yl | H | H | H | | | E |
| 10 | 4'-Methylpyridin-2'-yl | H | H | H | | | E |
| 11 | 4'-(Trifluoromethyl)pyridin-2'-yl | H | H | H | | | E |
| 12 | 4'-Methoxypyridin-2'-yl | H | H | H | | | E |
| 13 | 5'-Fluoropyridin-2'-yl | H | H | H | | | E |
| 14 | 5'-Chloropyridin-2'-yl | H | H | H | Oil | 7.47 | E |
| 15 | 5'-Bromopyridin-2'-yl | H | H | H | Oil | 7.47 | E |
| 16 | 5'-Methylpyridin-2'-yl | H | H | H | | | E |
| 17 | 5'-Methoxypyridin-2'-yl | H | H | H | | | E |
| 18 | 6'-Fluoropyridin-2'-yl | H | H | H | | | E |
| 19 | 6'-Chloropyridin-2'-yl | H | H | H | | | E |
| 20 | 6'-Bromopyridin-2'-yl | H | H | H | | | E |
| 21 | 6'-Methylpyridin-2'-yl | H | H | H | | | E |
| 22 | 6'-(Trifluoromethyl)pyridin-2'-yl | H | H | H | | | E |
| 23 | 6'-Methoxypyridin-2'-yl | H | H | H | | | E |
| 24 | 2'-Fluoropyridin-3'-yl | H | H | H | | | E |
| 25 | 2'-Chloropyrid-3'-yl | H | H | H | | | E |
| 26 | 2'-Bromopyrid-3'-yl | H | H | H | | | E |
| 27 | 2'-Methylpyridin-3'-yl | H | H | H | | | E |
| 28 | 2'-(Trifluoromethyl)pyridin-3'-yl | H | H | H | | | E |
| 29 | 2'-Methoxypyridin-3'-yl | H | H | H | | | E |
| 30 | 4'-Fluoropyridin-3'-yl | H | H | H | | | E |
| 31 | 4'-Chloropyridin-3'-yl | H | H | H | | | E |
| 32 | 4'-Bromopyridin-3'-yl | H | H | H | | | E |
| 33 | 4'-Methylpyridin-3'-yl | H | H | H | | | E |
| 34 | 4'-(Trifluoromethyl)pyridin-3'-yl | H | H | H | | | E |
| 35 | 4'-Methoxypyridin-3'-yl | H | H | H | | | E |
| 36 | 5'-Fluoropyridin-3'-yl | H | H | H | | | E |
| 37 | 5'-Chloropyridin-3'-yl | H | H | H | | | E |
| 38 | 5'-Bromopyridin-3'-yl | H | H | H | | | E |
| 39 | 5'-Methylpyridin-3'-yl | H | H | H | | | E |
| 40 | 5'-(Trifluoromethyl)pyridin-3'-yl | H | H | H | | | E |
| 41 | 5'-Methoxypyridin-3'-yl | H | H | H | | | E |
| 42 | 6'-Fluoropyridin-3'-yl | H | H | H | | | E |
| 43 | 6'-Chloropyridin-3'yl | H | H | H | | | E |
| 44 | 6'-Bromopyridin-3'-yl | H | H | H | | | E |
| 45 | 6'-Methylpyridin-3'-yl | H | H | H | | | E |
| 46 | 6'-(Trifluoromethyl)pyridin-3'-yl | H | H | H | | | E |
| 47 | 6'-Methoxypyridin-3'-yl | H | H | H | | | E |
| 48 | 2'-Fluoropyridin-4'-yl | H | H | H | | | E |
| 49 | 2'-Chloropyridin-4'-yl | H | H | H | | | E |
| 50 | 2'-Bromopyridin-4'-yl | H | H | H | | | E |
| 51 | 2'-Methylpyridin-4'-yl | H | H | H | | | E |
| 52 | 2'-(Trifluoromethyl)pyridin-4'-yl | H | H | H | | | E |
| 53 | 2'-Methoxypyridin-4'-yl | H | H | H | | | E |
| 54 | 3'-Fluoropyridin-4'-yl | H | H | H | | | E |
| 55 | 3'-Chloropyridin-4'-yl | H | H | H | | | E |
| 56 | 3'-Bromopyridin-4'-yl | H | H | H | | | E |
| 57 | 3'-Methylpyridin-4'-yl | H | H | H | | | E |
| 58 | 3'-(Trifluoromethyl)pyridin-4'-yl | H | H | H | | | E |
| 59 | 3'-Methoxypyridin-4'-yl | H | H | H | | | E |
| 60 | 4'-Fluoropyrimidin-2'-yl | H | H | H | | | E |
| 61 | 4'-Chloropyrimidin-2'-yl | H | H | H | | | E |
| 62 | 4'-Bromopyrimidin-2'-yl | H | H | H | | | E |
| 63 | 4'-Methylpyrimidin-2'-yl | H | H | H | | | E |
| 64 | 4'-(Trifluoromethyl)pyrimidin-2'-yl | H | H | H | | | E |
| 65 | 4'-Methoxypyrimidin-2'-yl | H | H | H | | | E |

TABLE II-continued

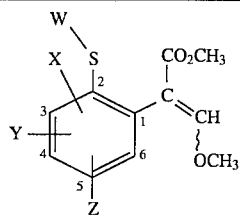

| Compound No. | W | X | Y | Z | Melting Point (°C.) | Olefinic* | Isomer + |
|---|---|---|---|---|---|---|---|
| 66 | 5'-Fluoropyrimidin-2'-yl | H | H | H | | | E |
| 67 | 5'-Chloropyrimidin-2'-yl | H | H | H | | | E |
| 68 | 5'-Bromopyrimidin-2'-yl | H | H | H | | | E |
| 69 | 5'-Methylpyrimidin-2'-yl | H | H | H | | | E |
| 70 | 5'-(Trifluoromethyl)pyrimidin-2'-yl | H | H | H | | | E |
| 71 | 5'-Methoxypyrimidin-2'-yl | H | H | H | | | E |
| 72 | 2'-Fluoropyrimidin-4'-yl | H | H | H | | | E |
| 73 | 2'-Chloropyrimidin-4'-yl | H | H | H | | | E |
| 74 | 2'-Bromopyrimidin-4'-yl | H | H | H | | | E |
| 75 | 2'-Methylpyrimidin-4'-yl | H | H | H | | | E |
| 76 | 2'-(Trifluoromethyl)pyrimidin-4'-yl | H | H | H | | | E |
| 77 | 2'-Methoxypyrimidin-4'-yl | H | H | H | | | E |
| 78 | 5'-Fluoropyrimidin-4'-yl | H | H | H | | | E |
| 79 | 5'-Chloropyrimidin-4'-yl | H | H | H | | | E |
| 80 | 5'-Bromopyrimidin-4'-yl | H | H | H | | | E |
| 81 | 5'-Methoxypyrimidin-4'-yl | H | H | H | | | E |
| 82 | 5'-(Trifluoromethyl)pyrimidin-4'-yl | H | H | H | | | E |
| 83 | 5'-Methoxypyrimidin-4'-yl | H | H | H | | | E |
| 84 | 6'-Fluoropyrimidin-4'-yl | H | H | H | | | E |
| 85 | 6'-Chloropyrimidin-4'-yl | H | H | H | | | E |
| 86 | 6'-Bromopyrimidin-4'-yl | H | H | H | | | E |
| 87 | 6'-Methylpyrimidin-4'-yl | H | H | H | | | E |
| 88 | 6'-(Trifluoromethyl)pyrimidin-4'-yl | H | H | H | | | E |
| 89 | 6'-Methoxypyrimidin-4'-yl | H | H | H | | | E |
| 90 | 2'-Fluoropyrimidin-5'-yl | H | H | H | | | E |
| 91 | 2'-Chloropyrimidin-5'-yl | H | H | H | | | E |
| 92 | 2'-Bromopyrimidin-5'-yl | H | H | H | | | E |
| 93 | 2'-Methylpyrimidin-5'-yl | H | H | H | | | E |
| 94 | 2'-(Trifluoromethyl)pyrimidin-5'-yl | H | H | H | | | E |
| 95 | 2'-Methoxypyrimidin-5'-yl | H | H | H | | | E |
| 96 | 4'-Fluoropyrimidin-5'-yl | H | H | H | | | E |
| 97 | 4'-Chloropyrimidin-5'-yl | H | H | H | | | E |
| 98 | 4'-Bromopyrimidin-5'-yl | H | H | H | | | E |
| 99 | 4'-Methylpyrimidin-5'-yl | H | H | H | | | E |
| 100 | 4'-(Trifluoromethyl)pyrimidin-5'-yl | H | H | H | | | E |
| 101 | 4'-Methoxypyrimidin-5'-yl | H | H | H | | | E |
| 102 | 5'-(Trifluoromethyl)pyridin-2'-yl | 4-F | H | H | | | E |
| 103 | 5'-(Trifluoromethyl)pyridin-2'-yl | H | H | H | Oil | 7.47 | E |
| 104 | 5'-Chloropyridin-2'-yl | 5-F | H | H | | | E |
| 105 | 5'-Chloropyridin-2'-yl | 3-F | 5-F | H | | | E |
| 106 | 5'-Chloropyridin-2'-yl | 4-F | 5-F | 6-F | | | E |
| 107 | 5'-Chloropyridin-2'-yl | 5-Cl | H | H | | | E |
| 108 | 5'-Chloropyridin-2'-yl | 5-CH$_3$O | H | H | | | E |
| 109 | 5'-Chloropyridin-2'-yl | 5-CH$_3$ | H | H | | | E |
| 110 | 5'-Fluoropyridin-2'-yl | 5-Cl | H | H | | | E |
| 111 | 5'-Fluoropyridin-2'-yl | 5-Cl | 3-F | H | | | E |

*Chemical shift of singlet from olefinic proton on beta-methoxyacrylate group (ppm from tetramethylsilane).
Solvent CDCl$_3$ (unless otherwise stated).
+ Geometry of beta-methoxyacrylate group.

TABLE III

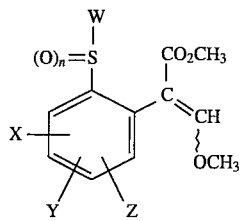

| Compound No. | W | n | X | Y | Z | Melting Point (°C.) | Olefinic* | Isomer + |
|---|---|---|---|---|---|---|---|---|
| 1 | 5'-Bromopyridin-2'-yl | 1 | H | H | H | gum | 7.60 | E |
| 2 | 5'-Bromopyridin-2'-yl | 2 | H | H | H | gum | 7.24 | E |
| 3 | 5'-Chloropyridin-2'-yl | 1 | H | H | H | | | E |
| 4 | 5'-Chloropyridin-2'-yl | 2 | H | H | H | | | E |
| 5 | 5'-(Trifluoromethyl)-pyridin-2'-yl | 1 | 5-F | H | H | | | E |

*Chemical shift of singlet from olefinic proton on beta-methoxyacrylate group (ppm from tetramethylsilane). Solvent $CDCl_3$ (unless otherwise stated).
+ Geometry of beta-methoxyacrylate group.

TABLE IV

Selected proton NMR data

Table IV shows selected proton NMR data for certain compounds described in Tables I, II and III and characterised therein as oils or gums. Chemical shifts are measured in ppm from tetramethylsilane, and deuterochloroform was used as solvent throughout. The following abbreviations are used:

| br = broad | t = triplet | ppm = parts per million |
|---|---|---|
| s = singlet | q = quartet | |
| d = doublet | m = multiplet | |

| Compound No. | |
|---|---|
| 10 (Table I) | 2.28 (3H,s); 3.52 (3H,s); 3.69 (3H,s); 6.77–7.98 (7H,m); 7.37 (1H,s) ppm. |
| 11 (Table I) | 3.57 (3H,s); 3.72 (3H,s); 7.0–7.4 (m); 7.44 (1H,s); 8.34 (H,d) ppm. |
| 16 (Table I) | 2.26 (3H,s); 3.56 (3H,s); 3.72 (3H,s); 6.65–7.98 (7H,m); 7.42 (1H,s) ppm. |
| 21 (Table I) | 2.40 (3H,s); 3.51 (3H,s); 3.67 (3H,s); 6.4–7.55 (7H,m); 7.4 (1H,s) ppm. |
| 22 (Table I) | 3.54 (3H,s); 3.74 (3H,s); 7.42 (1H,s) ppm. |
| 67 (Table I) | 3.60 (3H,s); 3.75 (3H,s); 7.20–7.4 (m); 7.40 (1H,s); 8.40 (2H,s) ppm. |
| 130 (Table I) | 3.85 (3H,s); 3.95 (3H,s); 7.44–7.84 (9H,m) ppm. |
| 131 (Table I) | 3.50 (3H,s); 3.60 (3H,s); 3.50 (2H br.s.); 7.40 (1H,s); 7.60 (1H,d) ppm. |
| 132 (Table I) | 3.70 (3H,s); 3.80 (3H,s); 7.55 (1H,s) ppm. |
| 133 (Table I) | 3.60 (3H,s); 3.75 (3H,s); 6.95 (1H,d); 7.45 (1H,s); 8.45 (1H,dd); 9.05 (1H,dd) ppm. |
| 137 (Table I) | 3.62 (3H,s); 3.76 (3H,s); 6.22 (1H,t); 7.20–7.50 (4H,m); 7.44 (1H,s) ppm. |
| 185 (Table I) | 3.52 (3H,s); 3.72 (3H,s); 7.14–7.38 (6H,m); 7.40 (1H,s); 8.36–8.38 (1H,m); 10.00 (1H,s). |
| 14 (Table II) | 3.60 (3H,s); 3.74 (3H,s); 6.68–6.72 (1H,d); 7.3–7.4 (4H,m); 7.47 (1H,s); 7.62–7.65 (1H,d); 8.34 (1H,s) ppm. |
| 15 (Table II) | 3.60 (3H,s); 3.74 (3H,s); 6.62–6.65 (1H,d); 7.3–7.5 (4H,m); 7.47 (1H,s); 7.62–7.64 (1H,d); 8.42 (1H,s) ppm. |
| 103 (Table II) | 3.60 (3H,s); 3.73 (3H,s); 6.78–6.82 (1H,d); 7.35-7.55 (4H,m); 7.47 (1H,s); 7.65–7.68 (1H,d); 8.6 (1H,s) ppm. |
| 165 (Table I) | 3.51 (3H,s); 3.69 (3H,s); 7.01 (1H,d); 7.23–7.46 (5H,m); 7.43 (1H,s); 7.62 (1H,t); 7.76 (1H,d); 7.85 (1H,d); 8.11 (1H,d) ppm. |
| 167 (Table I) | 3.64 (3H,s); 3.76 (3H,s); 6.31 (1H,d); 6.70 (1H,s); 7.11 (1H,d); 7.2–7.5 (4H,m) including 7.46 (1H,s) ppm. |
| 112 (Table II) | 3.60 (3H,s); 3.73 (3H,s); 6.78–6.82 (1H,d); 7.36–7.56 (4H,m); 7.47 (1H,s); 7.65–7.68 (1H,d); 8.60 (1H,s) ppm. |
| 1 (Table III) | 3.68 (3H,s); 3.87 (3H,s); 7.16–7.20 (1H,m); 7.42–7.45 (2H,m); 7.60 (1H,s); 7.76–7.79 (1H,d); 7.86–7.93 (2H,m); 8.47 (1H,s) ppm. |
| 2 (Table III) | 3.50 (3H,s); 3.55 (3H,s); 7.16–7.18 (1H,d); 7.24 (1H,s); 7.54–7.65 (2H,m); 8.00 (2H,s); 8.36–8.41 (1H,d); 8.63 (1H,s) ppm. |

The compounds of the invention having the general formula (I) can be prepared from substituted phenols or thiophenols of general formula (VII) by the steps shown in Scheme I. Throughout Scheme I the terms $R^1$, $R^2$, A, X Y, and W are as defined above, L is a halogen atom or another good leaving group which can sometimes be a nitro group and $R^8$ is hydrogen or a metal atom (such as a sodium atom).

Thus, compounds of general formula (I), which exist as geometric isomers which may be separated by chromatography, fractional crystallisation or distillation, can be prepared by treatment of phenylacetates of formula (IV) with a base (such as sodium hydride or sodium methoxide) and a formic ester such as methyl formate in a suitable solvent such as N,N-dimethylformamide and at a suitable temperature (step (b) of Scheme I). If a species of formula $R^2$-L, wherein L is as defined above, is then added to the reaction mixture, compounds of formula (I) may be obtained (step (a) of Scheme I). If a protic acid is added to the reaction mixture, compounds of formula (III) wherein $R^8$ is hydrogen are obtained. Alternatively, the species of formula (III) wherein $R^8$ is a metal atom (especially an alkali metal atom such as sodium atom) may themselves be isolated from the reaction mixture.

Compounds of formula (III) wherein $R^8$ is a metal atom can be converted into compounds of formula (I) by treatment with a species of formula $R^2$-L, wherein L is as defined above, in a suitable solvent. Compounds of formula (III) wherein $R^8$ is hydrogen can be converted into compounds of formula (I) by successive treatments with a base (such as potassium carbonate) and a species of general formula $R^2$-L, in a suitable solvent.

Alternatively, compounds of general formula (I) can be prepared from acetals of general formula (XIII) by elimination of the appropriate alkanol under either acidic or basic conditions, at a suitable temperature and often in a suitable solvent (step (c) of Scheme I). Examples of reagents or reagent mixtures which can be used for this transformation are lithium di-isopropylamide; potassium hydrogen sulphate (see, for example, T Yamada, H Hagiwara and H Uda, *J. Chem. Soc., Chemical Communications*, 1980, 838, and references therein); and triethylamine, often in the presence of a Lewis acid such as titanium tetrachloride (see, for example, K Nsunda and L Heresi, *J. Chem. Soc., Chemical Communications*, 1985, 1000).

Acetals of general formula (XIII) can be prepared by treatment of alkyl silyl ketene acetals of general formula (XIV), wherein R is an alkyl group, with a trialkyl orthoformate of formula $(R^2O)_3CH$ in the presence of a Lewis acid such as titanium tetrachloride, at a suitable temperature and in a suitable solvent (see, for example, K Saigo, M Osaki and T Mukaiyama, *Chemistry Letters*, 1976, 769).

Alkyl silyl ketene acetals of general formula (XIV) can be prepared from esters of general formula (IV) by treatment with a base and a trialkylsilyl halide of general formula $R_3SiCl$ or $R_3SiBr$, such as trimethylsilyl chloride, or a base and a trialkylsilyl triflate of general formula $R_3Si-OSO_2CF_3$, in a suitable solvent and at a suitable temperature (see, for example, C Ainsworth, F Chen and Y Kuo, *J. Organometallic Chemistry*, 1972, 46, 59).

It is not always necessary to isolate the intermediates (XIII) and (XIV); under appropriate conditions, compounds of general formula (I) may be prepared from esters of general formula (IV) in a "one pot" sequence by the successive addition of suitable reagents listed above.

Compounds of general formula (IV) can be prepared by esterification of compounds of general formula (V) by standard methods described in the chemical literature (Step (d) of Scheme I).

Compounds of general formula (V) can be prepared by the reaction of compounds of general formula (VII) with compounds of formula (VI) in the presence of a base (such as potassium carbonate) and, if necessary, a transition metal or transition metal salt catalyst (such as copperbronze) in a convenient solvent (such as N,N-dimethyl-formamide) (Step (e) of Scheme I).

Alternatively, compounds of general formula (IV) can be prepared from esters of general formula (VIII) by reaction with compounds of general formula (VI) in the presence of a base (such as potassium carbonate) and, if necessary, a transition metal or transition metal salt catalyst (such as copper-bronze) in a convenient solvent (such as N,N-dimethylformamide) (Step (f) of Scheme I).

Esters of general formula (VIII) can be prepared by esterification of compounds of general formula (VII) by standard methods described in the chemical literature (Step (g) of Scheme I).

Compounds of general formula (VII) can be prepared by standard methods described in the chemical literature. (For example, see, A. Clesse, W. Haefliger, D. Hauser, H. U. Gubler, B. Dewald and M. Baggiolini, *J.Med. Chem.*, 1981, 24, 1465) and P D Clark and D M McKinnon, *Can. J. Chem.*, 1982, 60, 243 and references therein).

Compounds of general formula (I) wherein A is sulphur may be converted into compounds of formula (I) wherein A is S(O) or $S(O)_2$ by standard methods of oxidation as described in the chemical literature, using, for example, a peracid such as meta-chloroperbenzoic acid, in a suitable solvent and at a suitable temperature.

Alternatively, compounds of the invention having the general formula (I) can be prepared from phenylacetates of general formula (XII) by the steps shown in Scheme II.

Throughout Scheme II the terms $R^1$, $R^2$, $R^8$, A, W, X Y, Z and L are as defined above, and M is a protecting group for a phenol or thiophenol group.

Thus compounds of general formula (I) can be prepared by reaction of compounds of general formula (IX) with compounds of general formula (VI) in the presence of a base (such as potassium carbonate) and, if necessary, a transition metal or transition metal salt catalyst in a convenient solvent (such as N,N-dimethylformamide) (step (h) of Scheme II).

Compounds of general formula (IX) can be prepared from protected phenol or thiophenol derivatives of general formula (X) by standard deprotection procedures as set out in the chemical literature (step (i) of Scheme II). For example, phenols of general formula (IX, A is O) can be prepared from benzyl ethers of general formula (X, A is O, M is $CH_2Ph$) by hydrogenolysis in the presence of a suitable catalyst (such as palladium supported on carbon).

Compounds of general formula (X), in which the group M is a standard phenol or thiophenol protecting group (such as benzyl), can be prepared by treatment of phenylacetates of formula (XII) with a base (such as sodium hydride or sodium methoxide) and a formic ester (such as methyl formate) in a suitable solvent such as N,N-dimethylformamide and at a suitable temperature (step (k) of Scheme II). If a species of formula $R^2$-L, wherein L is as defined above, is then added to the reaction mixture, compounds of formula (X) may be obtained (step (j) of Scheme II). If a protic acid is added to the reaction mixture, compounds of formula (XI) wherein $R^8$ is hydrogen are obtained. Alternatively, the species of formula (XI) wherein $R^8$ is a metal atom (especially an alkali metal atom such as a sodium atom) may themselves be isolated from the reaction mixture.

Compounds of formula (XI) wherein $R^8$ is a metal atom can be converted into compounds of formula (X) by treatment with a species of formula $R^2$-L, in a suitable solvent. Compounds of formula (XI) wherein $R^8$ is hydrogen can be converted into compounds of formula (X) by successive treatment with a base (such as potassium carbonate) and a species of formula $R^2$-L.

Compounds of general formula (XII) can be prepared from compounds of general formula (VIII) by standard methods described in the chemical literature.

Scheme I

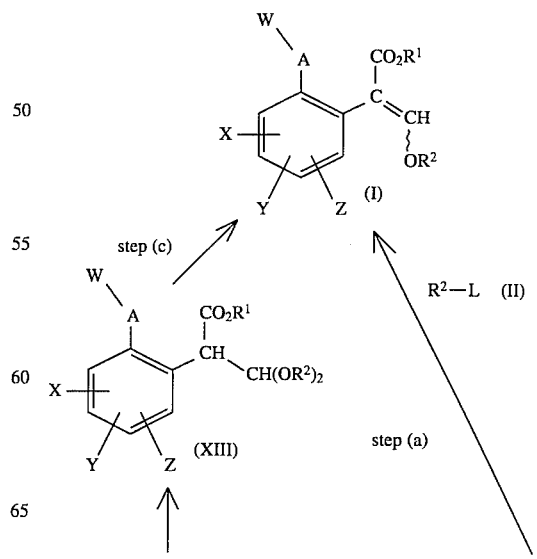

Scheme I -continued

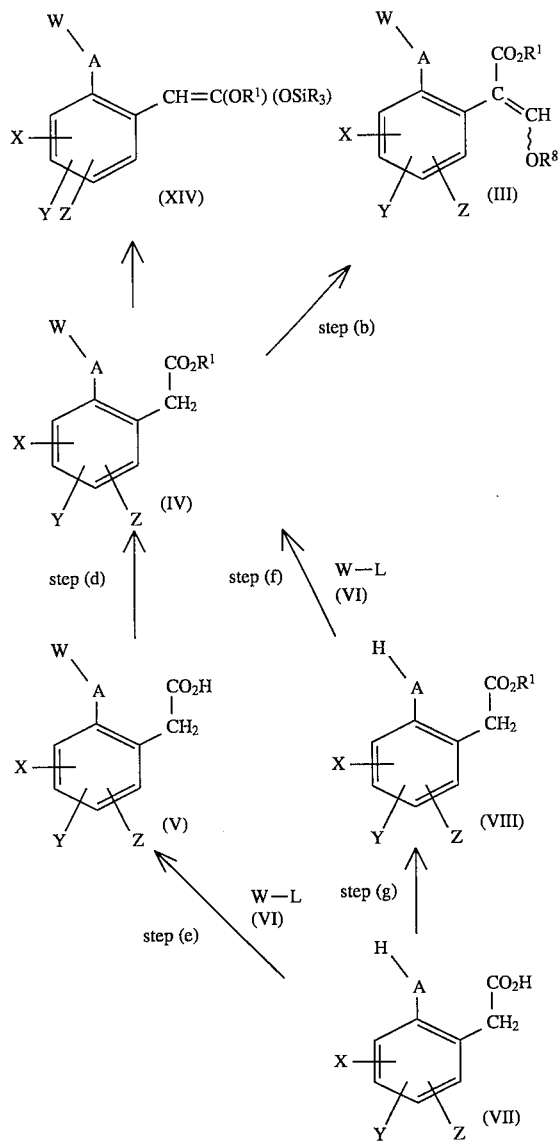

Scheme II

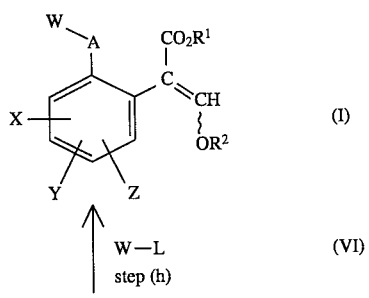

Scheme II -continued

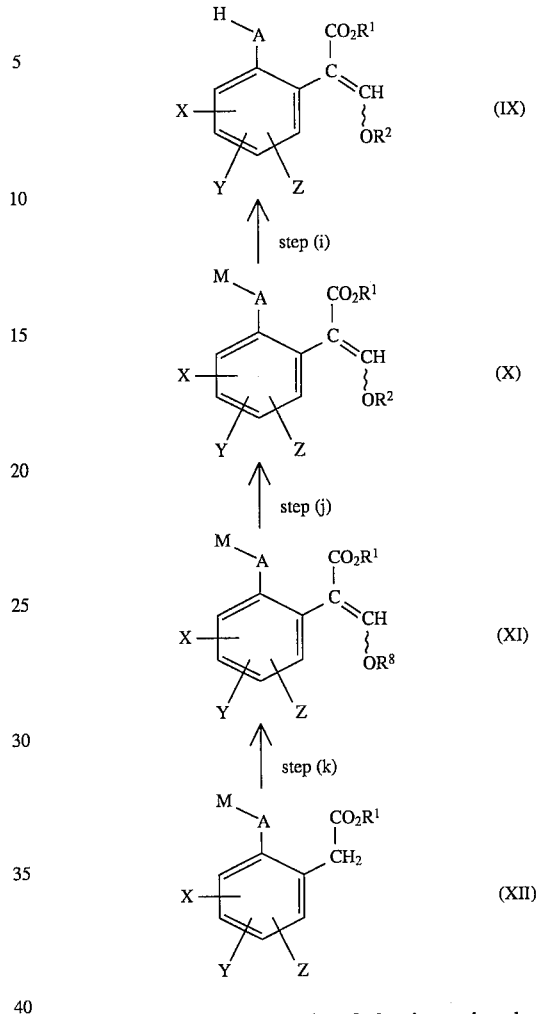

Alternatively, compounds of the invention having the general formula (I) can be prepared from substituted benzenes of general formula (XIX) by the steps shown in Scheme III. Throughout Scheme III the terms $R^1$, $R^2$, A, W, X, Y and Z are as defined above, D is hydrogen or halogen and E is a metal atom (such as a lithium atom) or a metal atom plus an associated halogen atom (such as MgI, MgBr or MgCl).

Thus, compounds of general formula (I) can be prepared by treatment of ketoesters of general formula (XV) with phosphoranes of general formula (XVI) in a convenient solvent such as diethyl ether (see, for example, EP-A-0044448 and EP-A-0178826 (Step (c) of Scheme III).

Ketoesters of general formula (XV) can be prepared by treatment of metallated species (XVII) with an oxalate (XVIII) in a suitable solvent such as diethyl ether or tetrahydrofuran. The preferred method often involves slow addition of a solution of the metallated species (XVII) to a stirred solution of an excess of the oxalate (XVIII) (see, for example, L M Weinstock, R B Currie and A V Lovell, *Synthetic Communications*, 1981, 11, 943, and references therein) (step (m) of Scheme III).

The metallated species (XVII) in which E is MgI, MgBr or MgCl (Grignard reagents) can be prepared by standard methods from the corresponding aromatic halides (XIX) in which D is I, Br or Cl respectively. With certain substituents X, Y and Z, the metallated species (XVII) in which E is Li can be prepared by direct lithiation of compounds (XIX) in which D is H using a strong lithium base such as n-butyllithium or lithium di-isopropylamide (see, for example, H W Gschwend and H R Rodriguez, *Organic Reactions*, 1979, 26, 1) (step (n)of Scheme III).

Compounds of general formula (XIX) can be prepared by standard methods described in the chemical literature.

Scheme III

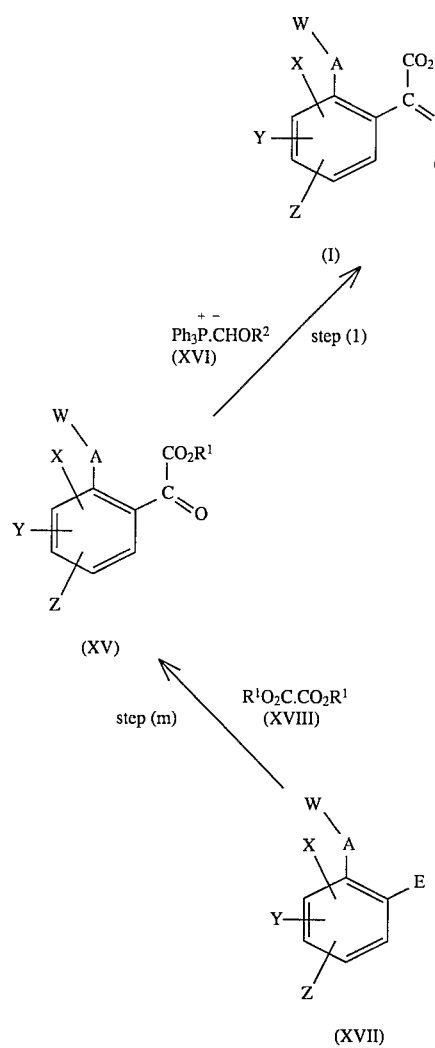

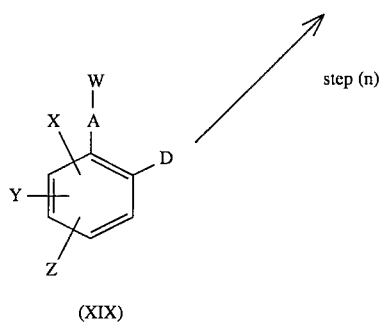

(XIX)

Alternative methods for the preparation of ketoesters of general formula (XV) are described in the chemical literature (see, for example, D C Atkinson, K E Godfrey, B Meek, J F Saville and M R Stillings, *J. Med. Chem.*, 1983, 26, 1353; D Horne, J Gaudino and W J Thompson, *Tetrahedron Lett.*, 1984, 25, 3529; and G P Axiotis, *Tetrahedron Lett.*, 1981, 22, 1509).

Methods for preparing compounds of the invention having the general formula (I), as described in Schemes I and II are generally applicable where W in general formula (I) is a substituted 2-pyridinyl, or a 2- or 4-pyrimidinyl group, and where W is a 4-pyridinyl group containing strong electron withdrawing substituents such as nitro, trifluoromethyl or fluoro. However for compounds of general formula (I) where W is a substituted 3- or 4-pyridinyl group the methods shown in Scheme II may not be generally applicable.

Also, although compounds of the invention having the general formula (I) where W is a substituted 3- or 4-pyridinyl group may be prepared from compounds of general formula (IV) by steps (a), (b) and (c) as shown in Scheme I, the preparation of compounds of general formula (IV) where W is a substituted 3- or 4-pyridinyl group may not be generally prepared by the steps (e) and (f) in Scheme I. Therefore an alternative method of preparation of compounds of general formula (IV) may need to be used.

In general, compounds of formula (IV) where W is a substituted 3- or 4-pyridinyl group, may preferably be prepared by the route shown in Scheme IV.

Thus, in Scheme IV compounds of formula (IV) where W is a substituted 3-or 4-pyridinyl group can be prepared from compounds of formula (XX) where W is a substituted 3- or 4-pyridinyl group.

Scheme IV

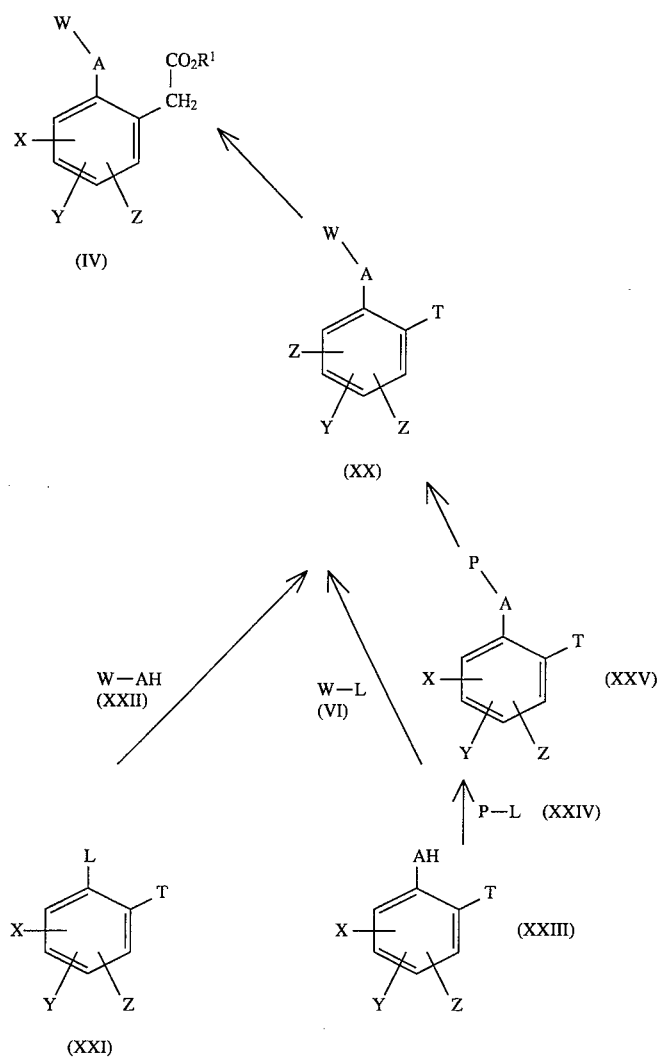

Throughout Scheme IV, A, X, Y, Z. and L are as defined above for Schemes I–III and T is any group that can be converted by standard methods in the literature. in one or more steps, into an acetic ester side chain of structure $CH_2COOR^1$ as shown in formula (IV). For example, T may be a formyl group or any group that is capable of being transformed into a formyl group, such as a formyl acetal which may be hydrolysed by aqueous acid to the formyl group or such as a nitrile which may be reduced to the formyl group by metal hydride reduction (see, for example, A E G Miller, J W Bliss and L H Schwartzmann, *J. Org. Chem.*, 1959, 24, 627) or by Raney Alloy in formic acid (see, for example, van Es and Staskun, *J. Chem. Soc.* 1965, 5775). When T is a formyl group, it may then be converted into the acetic ester residue $CH_2COOR^1$ by reaction with methyl methylsulphinylmethylsulphide ($CH_3SOCH_2SCH_3$) (see, for example, K Ogura and G Tsuchihashi, *Tetrahedron Lett.*, 1972, 1383–6), followed by hydrolysis with an alcohol $R^1OH$ in the presence of an acid such as hydrogen chloride. For example T may also be a group such as a methyl group which can be halogenated, for example by bromine or N-bromosuccinimide, to give a halomethyl group which can then be treated with cyanide ion to give a cyano methyl group, which in turn can be hydrolysed to the acetic ester residue $CH_2COOR^1$ by methods well known in the literature. T may also be for example a carboxylic acid or ester group which may be reduced to a hydroxymethyl group, which in turn can be converted to a cyanomethyl group by methods well known in the literature.

Compounds of formula (XX), where W is a substituted 3-pyridinyl group, can be prepared from compounds of formula (XXI), where L is defined as for Scheme I, by reaction with compounds of formula (XXII), where W is a substituted 3-pyridinyl group, under conditions generally used for the well known Ullmann synthesis. For example the compounds of formula (XXI) can be treated with the metal salt (preferably the sodium or potassium salt) of the compounds of formula (XXII), either neat or in a suitable solvent such as N,N-dimethylformamide or dimethylsulphoxide at 50°–250° C., but preferably at 100°–180° C., in the presence of a transition metal catalyst such as copper bronze or copper halides.

Compounds of general formula (XXI) can be prepared by standard methods in the chemical literature.

Compounds of formula (XX), where W is a substituted 4-pyridinyl group, can be prepared by reaction of the metal salt (preferably the sodium or potassium salt) of compounds of formula (XXIII) with compounds of formula (VI), where X is a substituted 4-pyridinyl group, in a suitable solvent such as N,N-dimethylformamide or dimethylsulphoxide at 20°–200° C., but preferably at 50°–150° C., and optionally in the presence of transition metal catalysts such as copper bronze or copper halides.

Compounds of formula (XX) may also be prepared from compounds of formula (XXV), where P is defined as a pyridine N-oxide linked to A through the 4-position. P may or may not be substituted by substituents as defined for W in compounds of formula (I). If P in compounds of formula (XXV) is substituted, then deoxygenation of the N-oxide by standard methods, for example with phosphorus trichloride, will give compounds of formula (XX) where W is substituted 4-pyridinyl. If P in compounds of formula (XXV) is substituted or unsubstituted, then the well known reaction of pyridine N-oxides with phosphoryl or thionyl halides can be used to give the compounds of formula (XX) containing an additional halogen atom in the 2- or 6-position, with concurrent loss of the N-oxide function, (see, for example, "The chemistry of the Heterocyclic Compounds: Pyridine and Its Derivatives", Ed. E Klingsberg, Part Two, p 121).

Compounds of formula (XXV) can be prepared by the reaction of the metal salt (preferably the sodium or potassium salt) of the compounds of formula (XXIII), with the compounds of formula (XXIV), wherein P and L are as defined above, in a suitable solvent such as N,N-dimethylformamide or dimethylsulphoxide, at 20°–200° C. but preferably at 50°–150°, optionally in the presence of a transition metal catalyst such as copper bronze or copper halides. Compounds of formula (XXIII) can be prepared by standard methods in the chemical literature.

In further aspects, the invention provides processes as herein described for preparing the compounds of the invention and the intermediate chemicals of formulae (III)–(V), (IX)–(XV), (XVII), (XIX), (XX), and (XXV) used therein.

The compounds are active fungisides, and may be used to control one or more of the following pathogens: *Pyricularia oryzae* on rice *Puccinia recondita, Puccinia striiformis* and other rusts on wheat, *Puccinia hordei, Puccinia striiformis* and other rusts on barley, and rusts on other hosts e.g. coffee, pears, apples, peanuts, vegetables and oranmental plants. *Erysiphe graminis* (powdery mildew) on barley and wheat and other powdery mildews on various hosts such as *Sphaerotheca macularis* on hops *Sphaerotheca fuliginea* on cucurbits (e.g. cucumber), *Podosphaera leucotricha* on apples and *Uncinula necator* on vines. Helminthosporium spp., Rhynchosporium spp., Septoria spp., *Pseudocercosporella herpotrichoides* and *Gaeumannomyces graminis* on cereals. *Cercospora arachidicola* and *Cercosporidium personata* on peanuts and other Cercospora species on other hosts for example sugar beet, bananas, soya beans and rice. *Botrytis cinerea* (grey mould) on tomatoes, strawberries, vegetables, vines and other hosts. Alternaria species on vegetables (e.g. cucumber), oil seed rape, apples, tomatoes and other hosts. *Venturia inaequalis* (scab) on apples *Plasmopara viticola* on vines. Other downy mildews such as *Bremia lactucae* on lettuce, Peronospora spp. on soybeans, tobacco, onions and other hosts and *Pseudoperonospora humuli* on hops and *Pseudoperonospora cubensis* on cucurbits *Phytophthora infestans* on potatoes and tomatoes and other Phytophthora spp. on vegetables, strawberries, avocado, pepper, ornamentals, tobacco, cocoa and other hosts. *Thanatephorus cucumeris* on rice and other Rhizoctonia species on various host such as wheat and barley, vegetables, cotton and turf.

Some of the compounds have also shown a broad range of activities against fungi in vitro. They may have activity against various post-harvest diseases of fruit (e.g. *Penicillium digitatum* and italicum and *Trichoderma viride* on oranges and *Gloesporium musarum* on bananas).

Further some of the compounds may be active as seed dressings against Fusarium spp., Septoria spp., Tilletia spp., (bunt, a seed borne disease of wheat), Ustilago spp., Helminthosporium. spp. on cereals, *Rhizoctonia solani* on cotton and *Pyricularia oryzae* on rice.

The compounds can move acropetally in the plant tissue. Moreover, they may be volatile enough to be active in the vapour phase against fungi on the plant.

Therefore in another aspect of the invention there is provided a method of combating fungi, which comprises applying to a plant, to seed of a plant, or to the locus of the plant or seed, an effective amount of a fungicidal compound of formula (I).

The compounds may also be useful as industrial (as opposed to agricultural) fungicides, e.g. in the prevention of fungal attack on wood, hides, leather and especially paint films.

Some of the compounds of the invention exhibit insecticidal and nematocidal activity.

Therefore in a further aspect of the invention there is provided a method of killing or controlling insect or nematode pests which comprises administering to the pest or to the locus thereof an effective amount of an insecticidal/nematocidal compound of formula (I).

A preferred group of compounds for use in this aspect of the invention are compounds of formula (I) where X is substituted pyridinyl wherein the substituents are preferably selected from halogen or haloalkyl.

Particularly preferred compounds for use in this method are compounds 14 and 15 in Table I.

Similarly, some compounds exhibit plant growth regulating activity and may be deployed for this purpose at appropriate rates of application. Therefore in yet a further aspect of the invention there is provided a method of regulating plant growth which comprises applying to a plant an effective amount of a plant growth regulating compound of formula (I).

The compounds may be used directly for agricultural purposes but are more conveniently formulated into compositions using a carrier or diluent. Therefore in yet a further aspect of the invention there are provided fungicidal, insecticidal/nematocidal and plant growth regulator compositions comprising a compound of general formula (I) as hereinbefore defined, and an acceptable carrier or diluent therefor.

As fungicides the compounds can be applied in a number of ways. For example they can be applied, formulated or unformulated, directly to the foliage of a plant, to seeds or to other medium in which plants are growing or are to be planted, or they can be sprayed on, dusted on or applied as a cream or paste formulation, or they can be applied as a vapour or as slow release granules. Application can be to any part of the plant including the foliage, stems, branches or roots, or to soil surrounding the roots, or to the seed before it is planted; or to the soil generally, to paddy water or to hydroponic culture systems. The invention compounds may also be injected into plants or sprayed onto vegetation using electrodynamic spraying techniques or other low volume methods.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dustable powders or granules comprising the active ingredient (invention compound) and a solid diluent or carrier, for example fillers such as kaolin, bentonite, kieselguhr, dolomite, calcium carbonate, talc, powdered magnesia, Fuller's earth, gypsum, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed may include an agent (for example a mineral oil) for assisting the adhesion of the composition to the seed; alternatively the active ingredient can be formulated for seed dressing purposes using an organic solvent (for example N-methylpyrrolidone, propylene glycol or dimethylformamide). The compositions may also be in the form of wettable powders or water dispersible granules comprising wetting or dispersing agents to facilitate the dispersion in liquids. The powders and granules may also contain fillers and suspending agents.

Emulsifiable concentrates or emulsions may be prepared by dissolving the active ingredient in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as isophorone, cyclohexanone, and methylcyclohexanone, chlorinated hydrocarbons such as benzyl alcohol, chlorobenzene and trichlorethane, and alcohols such as furfuryl alcohol, butanol and glycol ethers.

Suspension concentrates of largely insoluble solids may be prepared by ball or bead milling with a dispersing agent and including a suspending agent to stop the solid settling.

Compositions to be used as sprays may be in the form of aerosols wherein the formulation is held in a container under pressure in the presence of a propellant, e.g. fluorotrichloromethane or dichlorodi fluoromethane.

The invention compounds can be mixed in the dry state with a pyrotechnic mixture to form a composition suitable for generating in enclosed spaces a smoke containing the compounds.

Alternatively, the compounds may be used in a microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The invention compounds can be used as mixtures with fertilisers (e.g. nitrogen-, potassium-or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising a fertiliser and the compound of general formula (I) or a salt or metal complex thereof.

Wettable powders, emulsifiable concentrates and suspension concentrates will normally contain surfactants e.g. a wetting agent, dispersing agent, emulsifying agent or suspending agent. These agents can be cationic, anionic or non-ionic agents.

Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropyl-naphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10–85%, for example 25–60%, by weight of the active ingredient. After dilution to form aqueous preparations, such preparations may contain varying amounts of the active ingredient depending upon the intended purpose, but an aqueous preparation containing 0.0005% or 0.01% to 10% by weight of active ingredient may be used.

The compositions of this invention may contain other compounds having biological activity, e.g. compounds having similar or complementary fungicidal activity or which plant possess plant growth regulating, herbicidal or insecticidal activity.

A fungicidal compound which may be present in the composition of the invention may be one which is capable of combating ear diseases of cereals (e.g. wheat) such as Septoria, Gibberella and Helminthosporium spp., seed and soil borne diseases and downy and powdery mildews on grapes and powdery mildew and scab on apple etc. By including another fungicide, the composition can have a broader spectrum of activity than the compound of general formula (I) alone. Further the other fungicide can have a synergistic effect on the fungicidal activity of the compound of general formula (I). Examples of fungicidal compounds which may be included in the composition of the invention are carbendazim, benomyl, thiophanate-methyl, thiabendazole, fuberidazole, etridazole, dichlofluanid, cymoxanil, oxadixyl, ofurace, metalaxyl, furalaxyl, 4-chloro-N-(1-cyano-1-ethoxymethyl)benzamide, benalaxyl, fosetylaluminium, fenarimol, iprodione, prothiocarb, procymidone, vinclozolin, penconazole, myclobutanil, propamocarb, R0151297, diconazole, pyrazophos, ethirimol, ditalimfos, buthiobate, tridemorph, triforine, nuarimol, triazbutyl, guazatine, triacetate salt of 1,1'-iminodi(octamethylene) diguanidine, propiconazole, prochloraz, flutriafol, hexaconazole, (2 RS, 3 RS)-2-(4-chlorophenyl)-3-cyclopropyl-1-(1H-1,2,4-triazol-1-yl)butan-2-ol, (RS)-1-(4-chloro-phenyl) -4, 4-dimethyl-3- (1H-1, 2,4-triazol-1-ylmethyl)pentan-3-ol, flusilazole, triadimefon, triadimenol, diclobutrazol, fenpropimorph, pyrifenox, fenpropidin, chlorozolinate, imazalil, fenfuram, carboxin, oxycarboxin, methfuroxam, dodemorph, BAS 454, blasticidin S, kasugamycin, edifenphos, Kitazin P, cycloheximide, phthalide, probenazole, isoprothiolane, tricyclazole, pyroquilon, chlorbenzthiazone, neoasozin, polyoxin D, validamycin A, mepronil, flutolanil, pencycuron, diclomezine, phenazin oxide, nickel dimethyldithiocarbamate, techlofthalam, bitertanol, bupirimate, etaconazole, hydroxyisoxazole, streptomycin, cyprofuram, biloxazol, quinomethionate, dimethirimol, 1-(2-cyano-2-methoxyiminoacetyl)-3-ethyl urea, fenapanil, tolclofos-methyl, pyroxyfur, polyram, maneb, mancozeb, captafol, chlorothalonil, anilazine, thiram, captan, folpet, zineb, propineb, sulphur, dinocap, dichlone, chloroneb, binapacryl, nitrothalisopropyl, dodine, dithianon, fentin hydroxide, fentin acetate, tecnazene, quintozene, dicloran, copper containing compounds such as copper oxychloride, copper sulphate and Bordeaux mixture, and organomercury compounds.

The compounds of general formula (I) can be mixed with soil, peat or other rooting media for the protection of plants against seed-borne, soil-borne or foliar fungal diseases.

Suitable insecticides which may be incorporated in the composition of the invention include pirimicarb, dimethoate, demeton-s-methyl, formothion, carbaryl, isoprocarb, XMC, BPMC, carbofuran, carbosulfan, diazinon, fenthion, fenitrothion, phenthoate, chlorpyrifos, isoxathion, propaphos, monocrotophas, buprofezin, ethroproxyfen and cycloprothrin.

Plant growth regulating compounds are compounds which control weeds or seedhead formation, or selectively control the growth of less desirable plants (e.g. grasses).

Examples of suitable plant growth regulating compounds for use with the invention compounds are the gibberellins (e.g. $GA_3$, $GA_4$ or $GA_7$), the auxins (e.g. indoleacetic acid, indolebutyric acid, naphthoxyacetic acid or naphthylacetic acid), the cytokinins (e.g. kinetin, diphenylurea, benzimidazole, benzyladenine or benzylaminopurine), phenoxyacetic acids (e.g. 2,4-D or MCPA), substituted benzoic acid (e.g. triiodobenzoic acid), morphactins (e.g. chlorfluoroecol), maleic hydrazide, glyphosate, glyphosine, long chain fatty alcohols and acids, dikegulac, paclobutrazol, fluoridamid, mefluidide, substituted quaternary ammonium and phosphonium compounds (e.g. chloromequat chlorphonium or mepiquatchloride), ethephon, carbetamide, methyl-3,6-dichloroanisate, daminozide, asulam, abscisic acid, isopyrimol, 1-(4-chlorophenyl)-4,6-dimethyl-2-oxo-1,2-dihydropyridine-3-carboxylic acid, hydroxybenzonitriles (e.g. bromoxynil), difenzoquat, benzoylprop-ethyl 3,6-dichloropicolinic acid, fenpentezol, inabenfide, triapenthenol and tecnazene.

The following Examples illustrate the invention. Throughout these Examples, the term 'ether' refers to diethyl ether; chromatography was carried out using silica gel as the solid phase; magnesium sulphate was used to dry solutions; and reactions involving water- or air-sensitive intermediates were performed under nitrogen and in dried solvents. Where shown, infrared and NMR data are selective; no attempt is made to list every absorption. Unless otherwise stated, NMR spectra were recorded using deuterochloroform solutions. The following abbreviations are used throughout:

| | |
|---|---|
| g = gramme(s) | delta = chemical shift |
| mmol = micromole(s) | $CDCl_3$ = deuterochloroform |
| ml = milliliter(s) | s = singlet |
| mmHg = Millimeters pressure of mercury | d = doublet |
| | t = triplet |
| | br = broad |
| DMF = N,N-Dimethylformamide | |
| max. = maximum or maxima | |
| HPLC = High performance liquid chromatography | |
| mp. = Melting point | |
| ppm. = parts per million | |
| NMR = Nuclear magnetic resonance | |

EXAMPLE 1

This Example illustrates the preparation of (E)-methyl 2-[2'- (5"-chloropyridin-2"-yloxy)phenyl]-3-methoxyacrylate (Compound No. 14 of Table I).

A solution of 2,5-dichloropyridine (7.70 g, 52.03 mmol), potassium carbonate (14.01 g, 101.37 mmol) and the disodium salt derived from o-hydroxyphenylacetic acid (10.20 g, 52.58 mol) in dimethylsulphoxide (50 ml) was stirred overnight at 160° C. under an atmosphere of nitrogen. The dark reaction mixture was poured into water (100 ml), and extracted with ether (3×75 ml). The aqueous phase was acidified to pH 6 with concentrated hydrochloric acid and then extracted with ethyl acetate (3×100 ml). The combined organic layers were washed with brine (2×100 ml), dried and then evaporated under reduced pressure to give [2-(5'-chloropyridin-2'-yloxy)phenyl]acetic acid (5.30 g) as a dark brown liquid (infrared max. 3500–2700, 1700, 1370, 1440, 750 $cm^{-1}$) which was used without further purification. 2-(5'-Chloropyridin-2'-yloxy)phenylacetic acid (5.20 g, 19.73 mmol), potassium carbonate (5.53 g, 40 mmol) and dimethyl sulphate (2.91 g, 23.07 mmol) were stirred together overnight at room temperature in DMF (50 ml). The reaction mixture was poured into water (100 ml) and extracted with ethyl acetate (2×75 ml) and ether (1×100 ml). The combined organic layers were washed with water (3×75 ml) and brine (2×100 ml), and then dried and evaporated under reduced pressure to give methyl 2-(5'-chloropyridin-2'-yloxy)phenylacetate (4.18 g) as a dark brown liquid which was distilled at 152° C./0.1 mmHg.

To a stirred suspension of sodium hydride (0.78 g, 50% dispersion in oil) in DMF (40 ml) at −25° C. was added dropwise a solution of methyl 2-(5'-chloropyridin-2'-yloxy)phenylacetate (2.90 g, 10.45 mmol) and methyl formate (14.88 g, excess) in DMF. The reaction mixture was partitioned between saturated sodium carbonate solution and ether. The aqueous layer was acidified with concentrated hydrochloric acid to pH 4–5 (yellow precipitate) and then extracted with ethyl acetate (3×100 ml). The organic extracts were combined, dried and evaporated under reduced pressure to give methyl 2-[2'-(5"-chloropyridin-2"-yloxy)phenyl]-3-hydroxyacrylate as an orange-red solid (2.36 g). The solid (2.30 g, 7.54 mmol) was stirred overnight in DMF (50 ml) at room temperature with dimethyl sulphate (1.21 g, 9.59 mmol) and potassium carbonate (2.44 g, 17.6 mmol). The reaction mixture was poured into water (100 ml) and then extracted with ethyl acetate (3×100 ml). The combined organic layers were washed with water (3×75 ml) and brine (2×100 ml), and then dried and evaporated under reduced pressure to give a brown viscous liquid. HPLC (eluent ether—petroleum ether 50:50) gave a pale yellow liquid which crystallised on standing (2.14 g). Recrystallisation from methanol gave (E)-methyl 2-[2'-(5"-chloropyridin-2"-yloxyl)phenyl]-3-methoxyacrylate, m. p. 77°–8° C.; infrared max. 1700, 1625, 1260, 1200 $cm^{-1}$; $^1H$ NMR delta ($CDCl_3$) 3.57 (3H,s), 3.74 (3H,s), 6.75 (1H, d), 7.41 (1H,s), 8.10 (1H,brs), 7.1–7.6 (m) ppm.

EXAMPLE 2

This Example illustrates the preparation of (E)-methyl-2-[2',5"-cyanopyridin-2"-yloxy)phenyl]-3-methoxyacrylate (Compound No. 127 of Table I).

Ortho-hydroxyphenylacetic acid (3.08 g; 0.02 mol) was added to a stirred solution of potassium hydroxide (2.26 g, 0.04 mol) in methanol (40 ml). After 15 minutes the solution was evaporated to dryness under reduced pressure and the solid residue slurried in DMF (50 ml). 6-Chloronicotinonitrile (3.08 g; 0.022 mol) and copper bronze (0.1 g) was added and the mixture stirred at 80°–90° C. for 1 hour, then cooled and drowned into water (200 ml). The mixture was filtered and the pH of the filtrate was adjusted to 2–3 by addition of hydrochloric acid. The mixture was extracted with ether (×3). The combined ether extracts were extracted with saturated sodium bicarbonate solution. The aqueous phase was acidified with hydrochloric acid (pH 2–3) to produce a tarry solid. Trituration with a little methanol gave a white solid (1.27 g, 25% yield). Recrystallisation from water afforded 2-[2'-(5"-cyanopyridin-2"-yloxy)phenyl]acetic acid as a white solid mp. 120° C. Infrared max. 1672 cm$^{-1}$; $^1$H NMR (d$^6$ DMSO; 60MHz) delta 3.45 (2H,s); 7.05–7.45 (5H,m); 8.25–8.35 (m, 1H); 8.6 (1H,d); 6.3 (brs, 1H)ppm.

The acid (3.0 g, 0.0118 mol) was stirred at reflux in methanol (50 ml) containing concentrated sulphuric acid (0.1 ml) for 3 hours. The mixture was cooled, water (200 ml) was added and the mixture was extracted with ether (3×50 ml). The combined ether extracts were washed with saturated sodium bicarbonate solution (30 ml), water (3×30 ml) and saturated brine (1×30 ml). After drying and filtration the ether solution was evaporated to yield methyl 2-[2'-(5"-cyanopyridin-2"-yloxy)phenyl]acetate as an amber oil (2.77 g, 87.5% yield); infrared max. (thin film) 2200, 1700 cm$^{-1}$; $^1$H NMR (CDCl$_3$) 3.5 (5H, s); 6.8–7.3 (5H,m); 7.8 (1H,q); 8.3 (1H,d)ppm.

Trimethylsilyl trifluoromethylsulphonate (1.42 g; 0.0064 mol) was added dropwise to a solution of triethylamine (0.65 g; 0. 0064 mol) in diethyl ether (10 ml) at room temperature. The mixture was allowed to stand for 20 minutes then added dropwise over 15 minutes to a stirred solution of methyl 2-[2'-(5"-cyanopyridyloxy)phenyl]acetate (1.15 g; 0.0043 moles) in ether (10 ml) at 0°–5° C. The mixture was allowed to warm to room temperature and stirred for an hour to yield a two phase mixture. The upper layer (solution A) was retained.

Meanwhile, titanium tetrachloride (1.22 g, 0. 0064 mol) was added dropwise to a stirred solution of trimethyl orthoformate (0.71 g; 0.0064 mol) in dichloromethane (10 ml) at −70° C. The resulting yellow precipitate was stirred for 15 minutes and solution A was added dropwise over 20 minutes maintaining the temperature at −70° C. The mixture was stirred at −70° C. for 1 hour then allowed to warm to room temperature and stirred for 1 hour. Saturated sodium carbonate solution (50 ml) was added and the mixture was filtered. The filtrate was extracted with ether (3×20 ml). The combined organic extracts were washed with water (3×15 ml), saturated brine (15 ml) and after drying and filtration the ether solution was evaporated to dryness under reduced pressure. Chromatography of the residue (hexane/ether) gave the title compound as a glass which on trituration with methanol gave white crystals (40 mg, 3% yield) mp. 108.5°–109.5° C.: $^1$H NMR delta 3.58 (3H, s); 3.75 (3H, s); 6.9 (1H, d); 7.1 (1H, d); 7.28–7.4 (4H,m); 7.45 (1H,s); 7.85 (1H,q); 8.45 (1H,d) ppm.

EXAMPLE 3

This Example illustrates the preparation of (E)-methyl 2-[2'-(5"-nitropyridin-2"-yloxy)phenyl]-3-methoxyacrylate (Compound No. 133 of Table I).

2-(Hydroxyphenyl)acetic acid (50 g) was added to a solution of hydrogen chloride in methanol [prepared from acetyl chloride (25 ml) and methanol (250 ml)]. The solution was stirred at room temperature for three hours and then allowed to stand overnight (fifteen hours). The resulting mixture was concentrated under reduced pressure, and the residue was taken up in ether (250 ml) and washed with an aqueous solution of sodium bicarbonate until effervescence ceased. The ethereal solution was dried and then concentrated under reduced pressure and the resulting solid was recrystallized from ether/petrol to afford methyl (2-hydroxyphenyl)acetate (50 g; 92% yield) as white, powdery crystals, mp. 70°–72²⁰ C.; infrared max. (nujol mull): 3420, 1715 cm$^{-1}$; $^1$H nmr (90 MHz): delta 3.70 (2H,s), 3.75 (3H, s), 6.80–6.95 (2H,m), 7.05–7.10 (1H,m), 7.15–7.25 (1H,m), 7.40 (1H, s)ppm.

Methyl (2-hydroxyphenyl)acetate (21.0 g) was dissolved in DMF (200 ml), and potassium carbonate (19.35 g) was added in one portion. Benzyl bromide (23.94 g) in DMF (50 ml) was added dropwise to this mixture, with stirring, at room temperature. After eighteen hours the mixture was poured into water (500 ml) and extracted with ether (2×400 ml). The extracts were washed with water (3×150 ml) and brine (100 ml), dried and filtered through silica gel (50 g; Merck 60), then concentrated under reduced pressure to afford a yellow oil. Distillation at 160° C. and 0.05 mmHg afforded methyl 2-benzyloxyphenylacetate as a clear, colourless oil (26.99 g; 83% yield), infrared max. (film): 1730 cm$^{-1}$; $^1$H nmr (90 MHz): delta 3.60 (3H,s), 3.75 (2H,s), 4.10 (2H, s), 6.80–7.40 (9H,m)ppm.

A mixture of methyl 2-benzyloxyphenylacetate (26.99 g) and methyl formate (126.62 g) in dry DMF (300 ml) was added dropwise to a stirred suspension of sodium hydride (50% disp. in oil, 10.13 g) in DMF (300 ml) at 0° C. After stirring at 0° C. for two hours the mixture was poured into water (1000 ml) and washed with ether (2×150 ml). The aqueous layer was acidified to pH4 with 6M hydrochloric acid then extracted with ether (2×350 ml). The extracts were dried and concentrated under reduced pressure to afford crude methyl 2-[2'-benzyloxyphenyl]-3-hydroxyacrylate as a yellow oil, infrared max. (film): 1720, 1660 cm$^{-1}$.

The crude methyl 2-(2'-benzyloxyphenyl)-3-hydroxyacrylate was dissolved in dry DMF (100 ml) and potassium carbonate (29.0 g) was added in one portion. Dimethyl sulphate (16.00 g) in dry DMF (10 ml) was then added dropwise with stirring. After ninety minutes, water (300 ml) was added and the solution was extracted with ether (2×300 ml). After washing with water (3×150 ml) and brine, the extracts were dried and concentrated under reduced pressure, and the resulting yellow oil solidified on trituration with ether/petrol. Recrystallization from dry methanol afforded (E)-methyl 2-(2'-benzyloxyphenyl) -3-methoxyacrylate as a white, crystalline solid (5.44 g, 17% yield from methyl 2-benzyloxyphenylacetate), mp. 76–77° C.; infrared max. (nujol mull): 1710, 1640 cm$^{-1}$; $^1$H nmr (90 MHz): delta 3.63 (3H, s), 3.75 (3H, s), 5.05 (2H,s), 6.80–7.40 (9H,m), 7.50 (1H,s)ppm.

(E)-Methyl 2-(2'-benzyloxyphenyl)-3-methoxyacrylate (5.44 g) was dissolved in ethyl acetate (50 ml) and 5% palladium on carbon (0.25 g) was added. The stirred mixture was hydrogenated at three atmospheres pressure, with stirring, until no more hydrogen was taken up, then filtered through celite and silica gel (50 g, Merck 60). Concentration of the filtrate under reduced pressure afforded (E)-methyl 2-(2'-hydroxyphenyl)-3-methoxyacrylate as a white crystalline solid (3.76 g; 99% yield), mp. 125°–126° C.; infrared max. (nujol mull): 3400, 1670 cm$^{-1}$; $^1$H NMR (270 MHz): delta 3.80 (3H, s), 3.90 (3H, s), 6.20 (1H, s), 6.80–7.00 (2H,m), 7.10–7.30 (2H,m), 7.60 (1H, s)ppm.

(E)-Methyl 2-(2'-hydroxyphenyl) -3-methoxyacrylate (0.30 g, 1.44 mmol), 2-chloro-5-nitropyridine (0.46 g, 2.88 mmol) and potassium carbonate (0.40 g, 2.88 mmol) were stirred together in DMF (20 ml) at room temperature under an atmosphere of nitrogen. After 18 hours, the reaction mixture was poured into water and then extracted twice with ether. The combined ether layers were washed twice with water and brine, and then dried. The resultant solution was filtered through a plug of silica gel and then concentrated to afford a pink solid. Chromatography (eluent-ether) afforded (E)-methyl 2-[2'-(5"-nitropyridin-2"-yloxy)phenyl]-3-methoxyacrylate (240 mg) as a yellow gum which crystallised on standing, m.p. 107°–109° C.; $^1$H NMR: As Table IV.

EXAMPLE 4

This Example illustrates the preparation of (E)-methyl 2-[2'-(4"-chloropyrimidin-2"-yloxy)phenyl]-3-methoxyacrylate (Compound No. 61 of Table I).

E-Methyl 2-(2'-hydroxyphenyl)-3-methoxyacrylate (0.63 g), 2,4-dichloropyrimidine (0.75 g) and potassium carbonate (0.69 g) were stirred together in DMF at room temperature. After 2 hours the reaction mixture was poured into water (50 ml) and extracted twice with ether. The combined ether layers were washed with water (×3) and brine (×1) and then dried. Filtration and evaporation of the solvent under reduced pressure afforded a clear oil. Chromatography (eluent-ether) gave (E)-methyl 2-[2'-(4"-chloro-pyrimidin-2"-yloxy)phenyl]-3-methoxyacrylate (0.35 g) as an oil which crystallised on trituration with ether, m.p. 120°–121.5° C.: $^1$H NMR delta 3.60 (3H,s): 3.80 (3H,s); 6.60 (1H, d,J=4Hz); 7.40 (1H, s); 8.40 (1H, d,J=4Hz) ppm.

EXAMPLE 5

This Example illustrates the preparation of (E)-methyl 2-[2'-(5"-chloropyridin-2"-ylthio)phenyl]-3-methoxyacrylate (Compound No. 14 of Table II).

To a mixture of the disodium salt of o-mercaptophenylacetic acid (formed by treatment of o-mercaptophenylacetic acid (1.68 g) with sodium hydroxide (0.8 g) in methanol (10 ml) followed by evaporation of half of the resultant solution to dryness and re-dissolution in 10 ml of DMF) and copper-bronze was added a solution of 2,5dichloropyridine in DMF (5 ml). The reaction mixture was heated to 110°–120° C. for 90 minutes, added to water, acidified, and then extracted (×3) with ether. The combined ether layers were extracted with 2N sodium hydroxide (×1) and the resultant orange aqueous phase was acidified with dilute hydrochloric acid. The resulting suspension was filtered, and the solid was thoroughly washed with water and dried to give [2'-(5"-chloropyridin-2"-ylthio)phenyl]-acetic acid (0.88 g) as a fawn-coloured solid, m.p. 141°–4° C.

[2'-(5"-Chloropyridin-2"-ylthio)phenyl]acetic acid (0.65 g) was heated to reflux in methanol (15 ml) containing two drops of concentrated sulphuric acid. After 90 minutes, the solution was cooled to room temperature, poured into water and then extracted (×2) with ether. The combined organic phases were washed with 1M sodium hydroxide solution and water (×3) and then dried concentration under reduced pressure afforded methyl [2'-(5"-chloropyridin-2"-ylthio)phenyl]-acetate (610 mg) as a brown oil which was used without further purification.

To a stirred suspension of hexane-washed sodium hydride (0.144 g, 50% dispersion in oil) in DMF cooled to 2° C. (ice/salt bath) was added a solution containing methyl [2'-(5"-chloropyridin-2"-ylthio)phenyl]acetate (0.44 g) and methyl formate (1.8 g) in DMF (10 ml). The resultant reaction mixture was allowed to warm to room temperature. After 4½ hours, the reaction was quenched by careful addition of water, acidified with dilute hydrochloric acid, and then extracted (×3) with ether. The orange organic layers were combined, washed with water and then dried. Concentration under reduced pressure gave a crude mixture containing methyl 2-[2'-(5"-chloropyridin-2"-ylthio)phenyl]-3-hydroxyacrylate (0.40 g) as an orange gum (infrared max. 1665 cm$^{-1}$) which was used directly in the next stage. The orange gum was dissolved in DMF (10 ml) and potassium carbonate was added. The resulting suspension was cooled to 0° C. and then a solution of dimethyl sulphate in DMF (2 ml) was added dropwise over 5 minutes. After stirring at 0° C. for 1 hour, the reaction mixture was warmed to room temperature, poured into water and then extracted (33 4) with ethyl acetate. The combined organic phases were washed with water (×2) and then dried. Concentration under reduced pressure afforded a red oil (0.46 g) which was chromatographed (eluent-ether-hexane 1:1) to give the title compound (0.085 g) as a thick gum, infrared max. 1700, 1630 cm$^{-1}$, $^1$H NMR: As Table IV.

EXAMPLE 6

This Example illustrates the preparation of (E)-methyl 2-[2'-(5"-bromopyridin-2"-ylthio)phenyl]-3-methoxyacrylate (Compound No. 15 of Table II), (E)-methyl 2-(2'-(5"-bromo-pyridin-2"-ylsulphinyl)phenyl]-3-methoxyacrylate (compound No. 1 of Table III) and (E)-methyl 2-(2'-(5"-bromopyridin-2"-ylsulphonyl)phenyl]-3-methoxyacrylate (compound No. 2 of Table III).

(E)-Methyl 2-[2'-(5"-bromopyridin-2"-ylthio)phenyl]-3-methoxyacrylate (200 mg) prepared from 2,5-dibromopyridine following the procedure outlined in Example 5) was treated with meta-chloroperbenzoic acid (113 mg) in dry dichloromethane (10 ml) at 0° C. The orange solution became colourless within 15 minutes. After stirring for 30 minutes, the reaction mixture was partitioned with aqueous sodium hydrogen carbonate solution. The organic layer was washed with a second portion of aqueous sodium hydrogen carbonate solution and then with water and dried. The solvent was removed under reduced pressure to give a yellow gum (0.14 g)which was chromatographed (eluent ether) to afford (E)-methyl 2-[2'-(5"-bromopyrid-2"-ylsulphinyl)phenyl]-3-methoxyacrylate as a gum (30 mg); $^1$H NMR as Table IV; and (E)-methyl 2-(2'-(5"-bromopyrid-2"-ylsulphonyl)phenyl[-3-methoxyacrylate as an amorphous solid (30 mg); $^1$H NMR as Table IV.

EXAMPLE 7

This Example illustrates the preparation of (E)-methyl 2-[2'-5"-methoxycarbonylpyridin-2"-yloxy)phenyl]-3-methoxyacrylate (Compound No. 141 of Table I).

Methyl 2-[2'-5"-cyanopyridin-2"-yloxy)phenyl]acetic (2.03 g 0.008 mol; prepared as described in Example 2) was heated at reflux in a solution of potassium hydroxide (1.0 g; 0.017 mol) in water (30 ml) for 16 hours. The solution was cooled to room temperature and the pH was adjusted to 2–3 by the addition of hydrochloric acid. The resulting precipitate was filtered, washed with a little ice-cold water and dried at 95° C. (1.83 g). Recrystallisation from aqueous methanol afforded 2-[2'-(5"- carboxypyridin-2"-yloxy)phenyl]acetic acid (1.83 g) as white crystals; mp. 187°–188° C.; infrared max 3400, 2556, 1710, 1686 cm$^{-1}$; $^1$H NMR (d6 DMSO) delta 3.42 (2H, s); 6.32 (1H,brs); 6.95–7.44 (5H,m); 8.1 (1H,brs); 8.27 (1H, q); 8.62 (1H,d) ppm.

A mixture of 2-[2'-(5"-carboxypyrid-2"-yloxy)phenyl]acetic acid (1.46 g; 0.0053 mol), methyl iodide (1.52 g, 0.00107 mol), potassium carbonate (2.95 g; 0.021 mol) and DMF was stirred at room temperature for 3 hours. The mixture was drowned into water (100 ml) and extracted with ether (2×40 ml). The combined organic extract was washed with water (3×20 ml), and saturated brine (20 ml). After drying the filtration, evaporation of the ether solution gave methyl 2-[2'-(5"-methoxycarbonylpyridin-2"-yloxy)phenyl]acetate as an oil (0.73 g) $^1$H NMR delta 3.45 (3H, s); 3.47 (2H, s); 3.79 (3H,s); 6.73–7.3 (5H,m); 8.2 (1H,q); 8.7 (1H,d)ppm.

Trimethylsilyl trifluoromethanesulphonate (0.81 g; 0.0036 molar) was added dropwise to a solution of triethylamine (0.37 g, 0.0036 mol) in ether (10 ml) at room temperature. After standing for 20 minutes the resulting solution was added dropwise to a solution of methyl 2-[2'-(5-methoxycarbonyl)pyridin-2"-yloxy)phenyl]acetic in ether (10 ml) at 0°–5° C. over 20 minutes. The mixture was allowed to stir and warm to room temperature over 3 hours. The upper clear layer from this mixture was retained (solution A).

Meanwhile in a separate flask a solution of titanium tetrachloride (0.69 g, 0.0036 mol) in dichloromethane (5 ml) was added to a solution of trimethylorthoformate (0.4 g; 0.0036 mol) in dichloromethane (10 ml) at −70° C. The resulting yellow precipitate was stirred at −70° C. for 15 minutes. Solution A was added to the mixture dropwise over 10 minutes, maintaining the temperature at −70° C. The mixture was stirred for 1 hour, left to stand for 16 hours. Saturated sodium carbonate solution (50 ml) was added and the mixture was filtered. The filtrate was extracted with ether (3×20 ml) and the combined organic extracts were washed with water (3×15 ml) and saturated brine (15 ml). After drying and filtration the ether solution was evaporated to leave a tarry residue. The title compound was isolated as an oil from the residue by chromatography (eluent-hexane) (20 mg).

$^1$H NMR delta 3.47 (3H,s); 3.62 (3H, s); 3.82 (3H, s); 6.75–7.3 (5H,m); 7.32 (1H, s); 8.15 (1H,q); 8.72 (1H,d)ppm.

EXAMPLE 8

This Example illustrates the preparation of (E)-methyl 2-[2'-(5"-benzyloxycarbonylpyridin-2"-yloxy)phenyl]-3-methoxyacrylate (Compound No. 184 of Table I).

2-[2'-(5"-Carboxypyrid-2"-yloxy)phenyl]acetic acid (1.5 g; 0.005 molar; prepared as described in Example 7) was heated with methanol (50 ml) and sulphuric acid (0.1 ml) under reflux for 8 hours. The mixture was reduced to half bulk by evaporation, cooled, drowned into water (100 ml) and then extracted with ether (2×30 ml). The combined organic extracts were extracted with saturated sodium bicarbonate solution. The alkaline extract was acidified with hydrochloric acid to pH 2.3, cooled in ice-water and the resulting white precipitate was filtered, washed with water and dried at 95° C. to afford methyl 2-[2'-(5"-carboxypyridin-2"-yloxy)phenyl]acetate (0.63 g); mp. 118° C.; $^1$H NMR delta 3.52 (3H, s); 3.57 (2H, s); 6.88–7.4 (5H,m); 8.3 (1H,q); 8.88 (1H,d) ppm.

A mixture of methyl-2-[2'-(5"-carboxypyridin-2"-yloxy)phenyl]acetic (0.63 g; 0.0022 ml), benzyl bromide (0.37 g, 0.0021 moles), potassium carbonate (0.6 g; 0.0043 moles) and DMF (30 ml) was stirred at room temperature for 1 hour. The mixture was drowned into water (100 ml) and extracted with ether (2×30 ml). The combined organic extract was washed with water (3×15 ml) and saturated brine (15 ml). After drying and filtration, the ether solution was evaporated to give methyl 2-[2'-(5"-benzyloxycarbonylpyridin-2"-yloxy)phenyl]acetate as a colourless gum which was purified by chromatography (eluent/hexane) to give a colourless solid (0.69 g); mp. 56° C.; infrared max 1735, 1722 cm$^{-1}$, $^1$H NMR delta 3.44 (3H, s); 3.5 (2H, s); 5.24 (2H, s); 6.76–7.4 (5H,m); 8.2 (1H,q); 8.76 (1H,d) ppm.

Trimethylsilyl trifluoromethylsulphonate (0.61 g, 0.0027 moles) was added dropwise at room temperature to a solution of triethylamine (0.277 g; 0.0027 moles) in ether (5 ml). The mixture was allowed to stand for 20 minutes and the resulting solution was added to a stirred mixture of methyl 2-[2'-(5"-benzyloxycarbonylpyridin-2"-yloxy)phenyl]acetate in ether (5 ml) at 0°–5° C. over 15 minutes. The resulting mixture was allowed to stir and warm to room temperature over 3 hours then diluted with dichloromethane (5 ml) and retained (solution A).

Meanwhile a solution of titanium tetrachloride (0.52 g, 0.0027 moles) in dichloromethane (2 ml) was added dropwise to a solution of trimethylorthoformate (0.301 g; 0.0–077 moles) at −70° C. The resulting yellow precipitate was stirred at −70° C. for 15 minutes and solution A was added dropwise over 30 minutes, maintaining the temperature at −70° C. The mixture was stirred, allowed to warm to room temperature over 1 hour then left to stand for 15 hours. Saturated sodium carbonate solution (30 m) was added and the mixture was stirred, then filtered. The filtrate was extracted with ether (3×15 ml). The combined ether extracts were washed with water (3×10 m) and saturated brine (10 ml). After drying and filtration the ether solution was evaporated to give a gum. The title compound was isolated by chromatography (eluent-hexane) as a gum; $^1$H NMR delta 3.55 (3H, s); 3.60 (3H, s): 5.35 (2H, s); 6.82 (1H,d); 7.18–7.48 (m, including a one proton singlet at 7.39); 8.25 (1H,q); 8.25 (1H,d)ppm.

EXAMPLE 9

This Example illustrates the preparation of (E)-methyl 2-[2'-(6"-methylpyridin-3"-yloxy)phenyl]-3-methoxyacrylate (compound No. 45 of Table I).

6-Methyl-3-hydroxypyridine (9.5 g) was suspended in toluene (30 ml) and treated with aqueous potassium hydroxide [4.9 g in water (8 ml)]. The mixture was stirred vigorously for 15 minutes then evaporated under reduced pressure. Last traces of water were removed by repeated evaporation in the presence of toluene. The brown semisolid formed was treated with a combination of 2-(2-bromophenyl)-1,3-dioxolane (10.0 g), cuprous chloride (60 mg) and tris [2-(2-methoxyethoxy)ethyl]amine (0.194 g) to solubilise the copper salt, in dry DMF (25 ml) and the mixture was heated to 155° C. with stirring under nitrogen for 30 hours. Further cuprous chloride (60 mg) was added and heating continued for 14 hours.

The mixture was cooled, poured into water and extracted with ethyl acetate. The extract was washed with 2N aqueous sodium hydroxide solution and water, followed by extraction with 2N hydrochloric acid. The acidic aqueous extract was treated with solid potassium carbonate until pH 8 and then extracted with ethyl acetate. This organic extract was dried and then evaporated under reduced pressure to give 2-(6'-methylpyridin-3'-yloxy)benzaldehyde (2.2 g) as an oil; infrared maxima (film) 1697, 1606, 1480 cm$^{-1}$; $^1$H NMR delta 2.58 (3H, s); 6.86 (1H, s); 7.28 (3H,m); 7.55 (1H,t); 7.95 (1H,m); 8.36 (1H,m); 10.53 (1H, s) ppm.

2-(6'-Methylpyridin-3'-yloxy)benzaldehyde (2.08 g) and methyl methylsulphinylmethyl sulphide (1.21 g) were dissolved in dry THF (15 ml) and Triton B (1.5 ml) was added slowly dropwise with stirring at room temperature. The mixture was stood overnight, diluted with water and extracted with ethyl acetate. This extract was dried and then evaporated under reduced pressure, giving an orange-brown oil (3.2 g). The oil was treated with a methanol solution of hydrogen chloride (25 ml, 2.6N) and stood overnight at room temperature. The solution was then diluted with water and brought to pH 8 by the addition of sodium carbonate. The mixture was extracted with ethyl acetate and the extract dried and evaporated to give a brown oil (2.23 g) which was purified by HPLC (eluent 1:1, ethyl acetate: hexane) to give methyl [2-(6'-methylpyridin-3'-yloxy)phenyl]acetate, as a yellow oil (1.53 g) infrared maxima (film) 1747, 1488, 1237 cm$^{-1}$; $^1$H NMR delta 2.54 (3H, s); 3.63 (3H, s); 3.74 (2H, s); 6.84 (1H,d); 7.24 (5H,m); 8.3 (1H,d) ppm.

A mixture of methyl [2-(6'-methylpyridin-3'-yloxy)phenyl]acetate (1.3 g) and methyl formate (1.52 g) in DMF (5 ml) was added dropwise to a suspension of sodium hydride (316 mg of 50% oil dispersion) in DMF (5 ml), with stirring at 5° C. After stirring for 4 hours the mixture was diluted with water, made weakly acidic by addition of glacial acetic acid (pH 4–5) and extracted with ethyl acetate. This extract on drying and evaporation under reduced pressure, gave methyl 2-[2'-(6"-methylpyridin-3"-yloxy)phenyl]-3-hydroxyacrylate as a yellow oil (1.15 g) $^1$H NMR delta 2.53 (3H, s); 3.63 (3H, s) ; 6.89 (1H, s); 7.2 (5H,m); 8.21 (1H,d)ppm.

The oil (1.14 g) was dissolved in DMF (15 ml), potassium carbonate (1.1 g) was added and the mixture stirred for 15 minutes. Dimethyl sulphate (0.53 g)was dissolved in DMF (5 ml) and this solution added to the mixture. The resulting mixture was stirred for 30 minutes then diluted with water and the resulting emulsion extracted with ethyl acetate. This extract was dried and evaporated under reduced pressure to give a yellow oil (2.06 g), which was purified by HPLC (eluent ethyl acetate), to give (E)-methyl 2-[2'-(6"-methylpyridin-3"-yloxy)phenyl]-3-methoxyacrylate as a pale yellow oil (0.73 g), infrared maxima (film) 1705, 1642, 1488 cm$^{-1}$; $^1$H NMR delta 2.52 (3H, s); 3.63 (3H, s); 3.81 (3H,s); 6.88 (1H,d); 7.04–7.32 (5H,m); 7.51 (1H, s); 8.26 (1H, d)ppm.

The following are examples of compositions suitable for agricultural and horticultural purposes which can be formulated from the compounds of the invention. Such compositions form another aspect of the invention.

EXAMPLE 10

An emulsifiable concentrate is made up by mixing and stirring the ingredients until all are dissolved.

| Compound No. 61 of Table I | 10% |
| Benzyl alcohol | 30% |
| Calcium dodecylbenzenesulphonate | 5% |
| Nonylphenolethoxylate (13 moles ethylene oxide) | 10% |
| Alkyl benzenes | 45% |

EXAMPLE 11

The active ingredient is dissolved in methylene dichloride and the resultant liquid sprayed on to the granules of attapulgite clay. The solvent is then allowed to evaporate to produce a granular composition.

| Compound No. 14 of Table I | 5% |
| Attapulgite granules | 95% |

EXAMPLE 12

A composition suitable for use as a seed dressing is prepared by grinding and mixing the three ingredients.

| Compound No. 61 of Table I | 50% |
| Mineral oil | 2% |
| China clay | 48% |

EXAMPLE 13

A dustable powder is prepared by grinding and mixing the active ingredient with talc.

| Compound No. 61 of Table I | 5% |
| Talc | 95% |

EXAMPLE 14

A suspension concentrate is prepared by ball milling the ingredients to form an aqueous suspension of the ground mixture with water.

| Compound No. 61 of Table I | 40% |
| Sodium lignosulphonate | 10% |
| Bentonite clay | 1% |
| Water | 49% |

This formulation can be used as a spray by diluting into water or applied directly to seed.

EXAMPLE 15

A wettable powder formulation is made by mixing together and grinding the ingredients until all are thoroughly mixed.

| Compound No. 61 of Table I | 25% |
| Sodium lauryl sulphate | 2% |
| Sodium lignosulphonate | 5% |
| Silica | 25% |
| China clay | 43% |

EXAMPLE 16

The compounds were tested against a variety of foliar fungal diseases of plants. The technique employed was as follows.

The plants were grown in John Innes Potting Compost (No 1 or 2) in 4 cm diameter minipots. The test compounds were formulated either by bead milling with aqueous Dispersol T or as a solution in acetone or acetone/ethanol which was diluted to the required concentration immediately before use. For the foliage diseases, the formulations (100 ppm active ingredient) were sprayed onto the foliage and applied to the roots of the plants in the soil. The sprays were applied to maximum retention and the root drenches to a final concentration equivalent to approximately 40 ppm a.i./dry soil. Tween 20, to give a final concentration of 0.05%, was added when the sprays were applied to cereals.

For most of the tests the compound was applied to the soil (roots) and to the foliage (by spraying) one or two days before the plant was inoculated with the disease. An exception was the test on *Erysiphe graminis* in which the plants were inoculated 24 hours before treatment. Foliar pathogens were applied by spray as spore suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease control was recorded by the following grading:

4=no disease

3=trace –5% of disease on untreated plants

2=6–25% of disease on untreated plants

1=26–59% of disease on untreated plants

0=60–100% of disease on untreated plants

The results are shown in Table V.

TABLE V

| COMPOUND NUMBER | TABLE NO. | PUCCINIA RECONDITA (WHEAT) | ERYSIPHE GRAMINIS HORDEI (BARLEY) | VENTURIA INAEQUALIS (APPLE) | PYRICULARIA ORYZAE (RICE) |
|---|---|---|---|---|---|
| 10 | I | 4 | 4 | 4 | 4 |
| 11 | I | 3* | 4* | 4* | 2* |
| 14 | I | 4 | 4 | 2 | 4 |
| 15 | I | 4 | 4 | — | 3 |
| 16 | I | 2 | 4 | 4 | 4 |
| 21 | I | 3 | 4 | 4 | 4 |
| 22 | I | 4 | 4 | 4 | 4 |
| 61 | I | 3 | 4 | 4 | 0 |
| 67 | I | 3** | 2** | 0** | 0** |
| 129 | I | 0 | 4 | 4 | 0 |
| 130 | I | 3 | 0 | 0 | 0 |
| 131 | I | 3 | 0 | 0 | 0 |
| 133 | I | 4 | 4 | 4 | 4 |
| 137 | I | 2 | 0 | 4 | 0 |
| 138 | I | 4 | 0 | 3 | 0 |
| 139 | I | 4 | 0 | 0 | 2 |
| 140 | I | 2 | 0 | 0 | 0 |
| 165 | I | 2 | 4 | 4 | 2 |
| 166 | I | 4 | 4 | 4 | 1 |
| 167 | I | 4 | 4 | 4 | 3 |
| 14 | II | 4 | 4 | 4 | 3 |
| 15 | II | 2 | 3 | 0 | 0 |
| 1 | III | 0* | 0* | 3* | 0* |
| 2 | III | 3 | 0 | 3 | 0 |

| COMPOUND NUMBER | TABLE NO. | CERCOSPORA ARACHIDICOLA (PEANUT) | PLASMOPARA VITICOLA (VINE) | PHYTOPHTHORA INFESTANS (TOMATO) |
|---|---|---|---|---|
| 10 | I | 3 | 4 | 4 |
| 11 | I | 0* | 4* | 4* |
| 14 | I | 4 | 4 | — |
| 15 | I | 3 | 4 | — |
| 16 | I | 4 | 4 | 4 |
| 21 | I | 4 | 4 | 3 |
| 22 | I | 4 | 4 | 3 |
| 61 | I | 4 | 1 | 0 |
| 67 | I | 4** | 4** | 0** |
| 129 | I | 0 | 0 | 0 |
| 130 | I | 4 | 0 | 0 |
| 131 | I | 0 | 0 | 0 |
| 133 | I | — | 4 | 0 |
| 137 | I | 0 | 0 | 0 |
| 138 | I | 0 | 4 | 0 |
| 139 | I | 4 | 4 | 0 |
| 140 | I | 0 | 4 | 0 |
| 165 | I | 4 | 4 | 3 |
| 166 | I | 4 | 3 | 3 |
| 167 | I | 0 | 4 | — |
| 14 | II | 4 | 4 | 0 |
| 15 | II | 1 | 4 | 0 |
| 1 | III | 0* | 0* | 0* |
| 2 | III | 0 | 0 | 0 |

*25 ppm foliar spray only
**40 ppm foliar spray only

EXAMPLE 17

This Example illustrates the plant growth regulating properties of compounds 14–16, 22, 61, 132 and 138–140 of Table I.

These compounds were tested on a whole plant screen for plant growth regulating activity against six species of plant. The plant species used in this screen are presented in Table VI with the leaf stage at which they were sprayed.

A formulation of each chemical was applied at 4000 ppm (4 kg/ha in a 1000 l/ha field volume) using a tracksprayer and a SS8004E (Teejet) nozzle. Additional tests were done on tomatoes at 2000 and 500 ppm.

After spraying, the plants were grown in a glasshouse with 25° C. day/22° C. night temperatures. The exceptions to this were the temperate cereals, wheat and barley which were grown in 13°–16° C. day/11°–13° C. night temperatures. Supplementary lighting was supplied when necessary to provide an average photoperiod of 16 hours (14 hours minimum).

After 2–6 weeks in the glasshouse, depending on species and time of year, the plants were visually assessed for morphological characteristics against a control plant sprayed with a blank formulation. The results are presented in Table VII.

EXAMPLE 18

This Example illustrates the insecticidal properties of certain of the compounds of formula (I).

The activity of each compound was determined using a variety of insect mites and nematode pests. The compound was used in the form of liquid preparations containing from 100 to 500 parts per million (ppm) by weight of the compound. The preparations were made by dissolving the compound in acetone and diluting the solutions with water containing 0.1% by weight of a wetting agent sold under the trade name "SYNPERONIC" NX until the liquid preparations contained the required concentration of the product. "SYNPERONIC" is a Registered Trade Mark.

The test procedure adopted with regard to each pest was basically the same and comprised supporting a number of the pests on a medium which was usually a host plant or a food stuff on which the pests feed, and treating either or both the pests and the medium with the preparations. The mortality of the pests was then assessed at periods usually varying from one to seven days after the treatment.

The results of the tests are given in Table IX for each of the products, at the rate in parts per million given in the second column as a grading of mortality designated as 9, 5 or 0 wherein 9 indicates 80–100% mortality (70–100% root-knot reduction as compared to untreated plants for

TABLE VI

PLANT MATERIAL USED FOR WHOLE PLANT SCREEN

| Species | Code | Variety | Growth Stage at Treatment | No. Plants per 3" pot | Compost Type |
|---|---|---|---|---|---|
| Barley | BR | Atem | 1–1.5 leaves | 4 | JIP* |
| Wheat | WW | Timmo | 1–1.5 leaves | 4 | JIP |
| Maize | MZ | Earliking | 2¼–2½ leaves | 1 | PEAT |
| Apple | AP | Red Delicious | 4–5 leaves | 1 | JIP |
| Rice | RC | Ishikari | 2–2½ leaves | 4 | JIP |
| Tomato | TO | Ailsa Craig | 2–2½ leaves | 1 | PEAT |

JIP* John Innes Potting Compost.

TABLE VII

| Compound No. | Table | BR | WW | RC | AP | MZ | TO | TO* | TO+ |
|---|---|---|---|---|---|---|---|---|---|
| 14 | I | NT | NT | NT | NT | NT | NT | 2AT | 2AT |
| 15 | I | 1 | | | | 2A | NT | 1AT | 1AT |
| 16 | I | NT | NT | NT | NT | NT | 3A | NT | NT |
| 22 | I | NT | | NT | NT | 1A | NT | NT | NT |
| 61 | I | NT | NT | NT | 1 | NT | NT | 1 | |
| 132 | I | NT | | NT | NT | | NT | 1 | 1 |
| 138 | I | | | | | | 3 | NT | NT |
| 139 | I | | | | | | | NT | NT |
| 140 | I | | | | | | G | NT | NT |

KEY
*2000 ppm
+500 ppm
Retardation 1–3 where
1 = 10–30%
2 = 21–60%
3 = 61–100%
Greening effect = G
Apical damage = A
Tillering or side shooting = T
Blank means less than 10% effect
NT indicates that the compound was not tested against this species

*Meloidogyne incognita*, 5 indicates 50–79% mortality (50–69% root-knot reduction for *Meloidogyne incognita*) and 0 indicates less than 50% mortality (rootknot reduction for *Meloidogyne incognita*).

In Table IX the pest organism used is designated by a letter code and the pests species, the support medium or food, and the type and duration of test is given in Table VIII.

TABLE VIII

| CODE LETTERS | TEST SPECIES | SUPPORT MEDIUM/FOOD | TYPE OF TEST | DURATION |
|---|---|---|---|---|
| TUe | *Tetranychus uriticae* (spider mites and ova) | French bean leaf | Contact | 3 |
| CP | *Chilo partellus* (maize stem borers) | Oil seed rape leaf | Residual | 3 |
| DB | *Diabrotica balteata* (rootworm larvae) | Filter paper/ maize seed | Residual | 3 |
| MD | *Musca domestica* (houseflies-adults) | Cotton wool/ sugar | Contact | 1 |
| MI | *Meloidogyne incognita* (tomato root knot eelworm-larvae) | Semi in-vitro | Residual | 7 |

TABLE IX

| COMPOUND NO. | RATE OF APPLICATION | SPECIES (see Table VIII) | | | | |
|---|---|---|---|---|---|---|
| | | TUe | CP | DB | MD | MI |
| 14 | 500 | 0 | 9 | 5 | 9 | — |
| 15 | 500 | 0 | — | 9 | 0 | — |
|    | 250 | — | — | — | — | 9 |

We claim:

1. A compound having the formula (I):

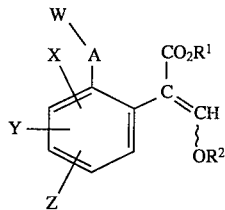

or a stereoisomer thereof, where W is a substituted pyrimidinyl group linked to A by any one of its carbon atoms; A is either an oxygen atom or $S(O)_n$ wherein n is 0, 1 or 2; X, Y and Z, which are the same or different, are hydrogen or halogen atoms, or hydroxy, optionally substituted alkyl, optionally substituted alkenyl, optionally substituted aryl, optionally substituted alkynyl, optionally substituted alkoxy, optionally substituted alkylthio, optionally substituted aryloxy, optionally substituted arylalkoxy, optionally substituted acyloxy, optionally substituted amino, optionally substituted acylamino, nitro, cyano, —$CO_2R^3$, —$CONR^4R^5$, —$COR^6$ or —$S(O)_mR^7$ (wherein m is 0, 1 or 2) groups, or any two of the groups X, Y and Z, when they are in adjacent positions on the phenyl ring join to form a fused ring, either aromatic or aliphatic; $R^1$ and $R^2$, which are the same or different, are optionally substituted alkyl groups; and $R^3$, $R^4$, $R^5$, $R^6$ and $R^7$ which are the same or different, are hydrogen atoms or optionally substituted alkyl, optionally substituted cycloalkyl, optionally substituted cycloalkylalkyl, optionally substituted alkenyl, optionally substituted alkynyl, optionally substituted aryl or optionally substituted aralkyl groups; and metal complexes thereof.

2. A compound according to claim 1 having the formula (I):

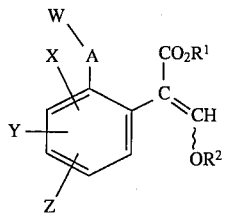

a stereoisomer thereof, where W is a substituted pyrimidinyl group linked to A by any one of its carbon atoms and bearing substituents selected from any of the values given for X, Y and Z in claim 1; A is either an oxygen atom or $S(O)_n$ wherein n is 0, 1 or 2; X, Y and Z, which are the same or different, are hydrogen, fluorine, chlorine or bromine atoms or hydroxy, $C_{1-4}$ alkyl, $C_{2-5}$ alkenyl, $C_{2-5}$ alkynyl, phenyl, $C_{1-4}$ haloalkyl, $C_{1-4}$ alkoxy, phenoxy, benzyloxy or mono- or dialkylamino groups, or any two of the groups X, Y and Z, when they are in adjacent positions on the phenyl ring, join to form a fused aromatic ring; wherein the aliphatic moieties of any of the foregoing are optionally substituted with one or more $C_{1-4}$ alkoxy groups, fluorine, chlorine or bromine atoms, phenyl rings which themselves are optionally substituted nitro, amino, cyano, hydroxyl or carboxyl groups, and wherein the phenyl moieties of any of the foregoing are optionally substituted with one or more fluorine, chlorine or bromine atoms, phenyl rings, $C_{1-4}$ alkyl, $C_{1-4}$ alkoxy, nitro, amino, cyano, hydroxyl or carboxyl groups; and $R^1$ and $R^2$, which are the same or different, are $C_{1-4}$ alkyl each optionally substituted with one, two or three halogen atoms.

3. A compound of the formula (Ia):

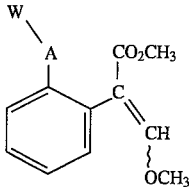

or a stereoisomer thereof, wherein A is $S(O)_n$ wherein n is 0, 1 or 2, or preferably an oxygen atom; W is a substituted pyrimidinyl group linked to A by any one of its carbon atoms, the substituents on the pyrimidinyl ring, which are the same or different, being one or more halogen atoms, or hydroxy, optionally substituted alkyl, optionally substituted alkenyl, optionally substituted aryl, optionally substituted alkynyl, optionally substituted alkoxy, (including haloalkoxy), optionally substituted aryloxy, optionally substituted aryl, optionally substituted acyloxy, optionally substituted amino, optionally substituted acylamino, nitro, cyano, —$CO_2R^3$, —$CONR^4R^5$, —$COR^6$ or $S(O)_mR^7$ (wherein m is 0, 1 or 2) groups.

4. The (E)-isomer of a compound according to claim 1 wherein A is oxygen.

5. A compound according to claim 1 wherein W is pyrimidinyl substituted by chlorine, fluorine, bromine, methyl, trifluoromethyl, trichloro methyl or methoxy.

6. A fungicidal composition comprising, as an active ingredient, a fungicidally effective amount of a compound according to claim 1 and a fungicidally acceptable carrier or diluent therefor.

7. A method of combating fungi which comprises applying to plants or seeds, or to their locus, a compound according to claim 1.

8. A plant growth regulating composition comprising, as an active ingredient, an effective amount of a plant growth regulating compound of formula I as defined in claim 1 and an acceptable carrier or diluent therefor.

9. A method of regulating plant growth which comprises applying to a plant an effective amount of a plant growth regulating compound of formula I according to claim 1.

10. An insecticidal/nematocidal composition comprising an insecticidal or nematocidal compound of formula I as defined in claim 1 in combination with a carrier or diluent.

11. A method of killing or controlling insect and nematode pests which comprises administering to the pest or to a locus thereof an effective amount of an insecticidal compound of formula I as defined in claim 1.

12. A compound having the formula (Ia):

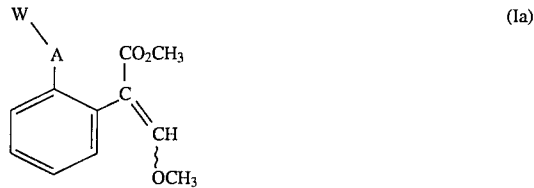

or a stereoisomer thereof, wherein A is $S(O)_n$ in which n is 0, 1 or 2, or an oxygen atom; W is a pyrimidinyl ring linked to A by any one of its carbon atoms and substituted by one or more substituents selected from the group comprising halogen, hydroxy, $C_{1-6}$ alkyl, $C_{2-6}$ alkenyl optionally substituted with phenyl, $C_{2-6}$ alkynyl, $C_{1-6}$ alkoxy, phenoxy, phenyl, —COR', —NR'R", —NHCOR', nitro, cyano, —$CO_2R^3$, —$CONR^4R^5$, —$COR^6$ or —$S(O)_mR^7$, wherein R' and R" are as defined below, $R^3$, $R^4$, $R^5$, $R^6$ and $R^7$, which are the same or different, are hydrogen, $C_{1-6}$ alkyl, cycloalkyl, $C_{3-6}$ cycloalkyl($C_{1-4}$)alkyl, $C_{2-6}$ alkenyl, $C_{2-6}$ alkynyl, phenyl or phenyl($C_{1-6}$)alkyl and m is 0, 1 or 2, any of the foregoing alkyl and alkoxy moieties being optionally substituted with halogen, hydroxy, $C_{1-6}$ alkoxy, phenyl or phenoxy, any of the foregoing phenyl moieties being optionally substituted with halogen, hydroxy, $C_{1-4}$ alkyl, $C_{1-4}$ alkoxy, halo($C_{1-4}$)alkyl, halo($C_{1-4}$)alkoxy, $C_{1-4}$ alkylthio, $C_{1-4}$ alkoxy($C_{1-4}$)alkyl, $C_{3-6}$ cycloalkyl, $C_{3-6}$ cycloalkyl ($C_{1-4}$) alkyl, phenyl, phenoxy, phenyl ($C_{1-4}$) alkyl, phenyl ($C_{1-4}$) alkoxy, phenoxy($C_{1-4}$) alkyl, cyano, thiocyanato, nitro, —NR'R", —NHCOR', —NHCONR'R", —CONR'R", —COOR', —OSO$_2$R', —SO$_2$R', —COR', OCOR', —CR'=NR" or N=CR'R" wherein R' and R" are independently hydrogen, $C_1$ alkyl, $C_{1-4}$ alkoxy, $C_{1-4}$ alkylthio, $C_{3-6}$ cycloalkyl, $C_{3-6}$ cycloalkyl ($C_{1-4}$)alkyl, phenyl or benzyl the phenyl and benzyl groups being optionally substituted with halogen, $C_{1-4}$ alkyl, or $C_{1-4}$ alkoxy.

13. A compound according to claim 12 wherein A is oxygen.

14. The (E)-isomer of a compound according to claim 12.

* * * * *